United States Patent
Jackson et al.

(10) Patent No.: US 9,670,436 B2
(45) Date of Patent: Jun. 6, 2017

(54) CLEANING COMPOSITIONS COMPRISING AMYLASE VARIANT REFERENCE TO A SEQUENCE LISTING

(71) Applicant: The Procter & Gamble Company, Cincinnati, OH (US)

(72) Inventors: Michelle Jackson, Tyne & Wear (GB); Philip Frank Souter, Northumberland (GB); Lindsay Suzanne Bewick, Tyne & Wear (GB); Svend Kaasgaard, Skovlunde (DK); Jens Oebro, Humlebaek (DK); Signe Eskildsen Larsen, Kongens Lyngby (DK); Allan Svendsen, Hoersholm (DK); Annette Helle Johansen, Broenshoej (DK); Michael Skjoet, Jyllinge (DK); Carsten Andersen, Vaerloese (DK); Lars Beier, Soeborg (DK); Esben Peter Friis, Herlev (DK); Miguel Duarte Guilherme Pereira Toscano, Frederiksberg (DK); Mads Bjoernvad, Virum (DK); Frank Winther Rasmussen, Roskilde (DK); Liv Spaangner Christiansen, Gentofte (DK)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/014,048

(22) Filed: Feb. 3, 2016

(65) Prior Publication Data
US 2016/0177238 A1 Jun. 23, 2016

Related U.S. Application Data

(63) Continuation of application No. 13/537,606, filed on Jun. 29, 2012, now Pat. No. 9,284,544.

(30) Foreign Application Priority Data

Jun. 30, 2011 (EP) .................................... 11172288

(51) Int. Cl.
- *C12N 9/28* (2006.01)
- *C12N 15/00* (2006.01)
- *C11D 3/386* (2006.01)
- *A61K 38/00* (2006.01)

(52) U.S. Cl.
CPC .......... *C11D 3/386* (2013.01); *C11D 3/38681* (2013.01); *C12N 9/2417* (2013.01); *C12Y 302/01001* (2013.01)

(58) Field of Classification Search
CPC ....... C12N 9/2414; C12N 15/00; C12N 15/09
See application file for complete search history.

(56) References Cited

U.S. PATENT DOCUMENTS

| | | | |
|---|---|---|---|
| 5,856,164 A | 1/1999 | Outtrup et al. | |
| 6,093,562 A | 7/2000 | Bisgaard-Frantzen | |
| 6,623,948 B1 | 9/2003 | Outtrup et al. | |
| 6,743,616 B2 | 6/2004 | Araki et al. | |
| 7,432,099 B2 | 10/2008 | Andersen et al. | |
| 7,541,026 B2 | 6/2009 | Power et al. | |
| 8,883,970 B2 | 11/2014 | Anderson et al. | |
| 9,284,544 B2 * | 3/2016 | Jackson | C11D 3/386 |
| 2001/0039253 A1 | 11/2001 | Borchert et al. | |
| 2003/0171236 A1 | 9/2003 | Svendsen et al. | |
| 2007/0190632 A1 * | 8/2007 | Bessler | C12N 9/2417 435/183 |
| 2007/0212768 A1 * | 9/2007 | Bessler | C12N 9/2417 435/186 |
| 2008/0193999 A1 | 8/2008 | Andersen et al. | |
| 2009/0314286 A1 | 12/2009 | Cuevas et al. | |
| 2011/0195481 A1 | 8/2011 | Svendsen et al. | |
| 2011/0212876 A1 | 9/2011 | Meek et al. | |
| 2012/0045817 A1 | 2/2012 | Estell et al. | |
| 2012/0045822 A1 | 2/2012 | Concar et al. | |
| 2013/0000055 A1 | 1/2013 | Jackson et al. | |

FOREIGN PATENT DOCUMENTS

| | | |
|---|---|---|
| EP | 1 707 624 A2 | 10/2006 |
| WO | WO 98/05748 A1 | 2/1998 |
| WO | WO 99/23211 A1 | 5/1999 |
| WO | WO 00/60058 | 10/2000 |
| WO | WO 02/092797 A2 | 11/2002 |
| WO | WO2013/001078 A1 | 1/2013 |
| WO | WO/2013001087 A2 | 1/2013 |

OTHER PUBLICATIONS

Huang, N., et al., 1990, "Structural organization and differential expression of rice alpha-amylase genes", Nucleic Acids Research, vol. 18, pp. 7007-7014.*
O'Neill, S.D., et al., 1990, "The alpha-amylase genes in Oryza sativa: characterization of cDNA clones and mRNA expression during seed germination", Molecular and General Genetics, vol. 221, pp. 235-244.*
R. Kanan: "Role of Trp140 at subsite-6 on the maltohexaose production of maltohexaose-producing amylase from alkalophilic *Bacillus* sp. 707", Protein Science, vol. 15, No. 3, Jan. 1, 2006, pp. 468-477.
International Search Report for application No. PCT/US2012/044757, dated Sep. 11, 2012, containing 8 pages.
Tsukamoto A., et al., 1988, "Nucleotide sequence of the maltohexaose-producing amylase gene from an alkalophilic *Bacillus* sp.U #707 and structural similarity to liquefying type alpha-amylases", Biochemical and Biophysical Research Communications, vol. 151, No. 1, pp. 25-31.
DeClerck, N., et al., 2002, "Engineering the thermostability of Bacillus licheniformis alpha-amylase", Biologia, Bratislava, vol. 57, Supplement 11, pp. 203-211.

(Continued)

*Primary Examiner* — Anand Desai
*Assistant Examiner* — Samuel Liu
(74) *Attorney, Agent, or Firm* — Melissa Krasovec; Leonard W. Lewis; Steven W. Miller

(57) ABSTRACT

The present invention relates to cleaning compositions comprising variants of an alpha-amylase and methods of treating surfaces such as textiles with aqueous liquor comprising such compositions, especially at low temperatures.

20 Claims, No Drawings

(56) References Cited

OTHER PUBLICATIONS

Davies, G.J., et al., 2005, "Structure of a Bacillus halmapalus family 13 alpha-amylase, BHA, in complex with an acarbosederived nonasaccharide at 2.1 A resolution", Acta Crystallographica D, vol. 61, pp. 190-193.

* cited by examiner

CLEANING COMPOSITIONS COMPRISING AMYLASE VARIANT REFERENCE TO A SEQUENCE LISTING

CROSS-REFERENCES TO RELATED APPLICATION

This application is a continuation of U.S. application Ser. No. 13/537,606, now U.S. Pat. No. 9,284,544, filed Jun. 29, 2012 which in turn claims priority to European Patent Application EP 11172288.0, filed Jun. 30, 2011.

REFERENCE TO A SEQUENCE LISTING

This application contains a Sequence Listing in computer readable form. The computer readable form is incorporated herein by reference.

FIELD OF THE INVENTION

The present invention relates to cleaning compositions comprising variants of an alpha-amylase having improved cleaning performance relative to its parent amylase in cold water surface treatment processes.

BACKGROUND OF THE INVENTION

Alpha-amylases (alpha-1,4-glucan-4-glucanohydrolases, E.C. 3.2.1.1) constitute a group of enzymes, which catalyse hydrolysis of starch and other linear and branched 1,4-glucosidic oligo- and polysaccharides.

Among the first bacterial alpha-amylases to be used were an alpha-amylase from *B. licheniformis*, also known as Termamyl which has been extensively characterized and the crystal structure has been determined for this enzyme. Alkaline amylases, such as the alpha-amylase derived from *Bacillus* sp. as disclosed in WO 95/26397, form a particular group of alpha-amylases that have found use in detergents. Many of these known bacterial amylases have been modified in order to improve their functionality in a particular application.

Methods of increasing the thermostability of alpha-amylases have been well studied. Suzuki et al. (1989) disclose chimeric alpha-amylases, in which specified regions of a *B. amyloliquefaciens* alpha-amylase have been substituted for the corresponding regions of a *B. licheniformis* alpha-amylase. The chimeric alpha-amylases were constructed with the purpose of identifying regions responsible for thermostability. Such regions were found to include amino acid residues 177-186 and amino acid residues 255-270 of the *B. amyloliquefaciens* alpha-amylase. Igarashi et al. 1998 show that the thermostability of AmyS-type amylases can be increased by the deletion of two amino acid residues, R179-G180, (AmyS numbering) from a loop (F 178 to A184). However, Shiau et al. (2003) showed that an AmyS enzyme with deletion in the same loop has a lower specific activity for corn starch hydrolysis at high-temperature than the parent enzyme, negating one of the principal advantages of AmyS amylases.

For environmental reasons it has been increasingly important to lower the temperature in washing, dishwashing and/or cleaning processes. However, most enzymes including amylases have a temperature optimum which is above the temperature usually used in low temperature washing. Alpha-amylase is a key enzyme for use in detergent compositions and its use has become increasingly important for removal of starchy stains during laundry washing or dishwashing. Therefore, it is important to find alpha-amylase variants, which retain their wash performance, stain removal effect and/or activity when the temperature is lowered. However, despite the efficiency of current detergents enzyme compositions, there are many stains that are difficult to completely remove. These problems are compounded by the increased use of low (e.g., cold water) wash temperatures and shorter washing cycles. Thus, it is desirable to have amylolytic enzymes that can function under low temperature and at the same time preserve or increase other desirable properties such as specific activity (amylolytic activity), stability and/or wash performance.

Thus it is an object of the present invention to provide cleaning compositions comprising alpha-amylases variants which can be used in washing, dishwashing and/or cleaning processes at low temperature, such as temperatures of 5-35° C. It is a further object of the present invention to provide alpha-amylase variants which have improved wash performance at low temperature compared to the parent alpha-amylase or compared to the alpha-amylase of any of SEQ ID NO: 1, 2, 3, 4, 5, 6, 7, 8, 9, 10, 11 or 12.

SUMMARY OF THE INVENTION

In a first aspect the invention provides a cleaning composition comprising:
(a) a variant of a parent alpha-amylase, comprising an alteration at two or more (several) positions corresponding to positions G304, W140, W189, D134, E260, F262, W284, W347, W439, W469, G476, and G477 of the mature polypeptide of SEQ ID NO: 1, wherein each alteration is independently a substitution, deletion or insertion, and wherein the variant has at least 80% or at least 87%, but less than 100% sequence identity with the mature polypeptide of any of SEQ ID NOs 1, 2, 3, 4, 5, 6, 7, 8, 9, 10, 11 or 12, and wherein the variant has alpha-amylase activity;
(b) and a cleaning adjunct, preferably in an amount from 0.01 to 99.9 wt %.

The invention also provides a method of treating a surface, preferably a textile, comprising (i) forming an aqueous wash liquor comprising water and a cleaning composition comprising; and
(a) a variant of a parent alpha-amylase, comprising an alteration at two or more (several) positions corresponding to positions G304, W140, W189, D134, E260, F262, W284, W347, W439, W469, G476, and G477 of the mature polypeptide of SEQ ID NO: 1, wherein each alteration is independently a substitution, deletion or insertion, and wherein the variant has at least 80%, or at least 87%, but less than 100% sequence identity with the mature polypeptide of any of SEQ ID NOs 1, 2, 3, 4, 5, 6, 7, 8, 9, 10, 11 or 12, and wherein the variant has alpha-amylase activity; and
(b) a cleaning adjunct, preferably in an amount from 0.01 to 99.9 wt %;
(ii) treating the surface with the aqueous wash liquor preferably at a temperature of 40° C. or less, or more preferably at a temperature of 30° C. or less, most preferably at a temperature of 20° C. or less; and (iii) rinsing the surface.

In accordance with a further aspect of the invention there is provided cleaning composition comprising: a variant a variant of a parent alpha-amylase, comprising an alteration at two or more (several) positions corresponding to positions G304, W140, W189, D134, E260, F262, W284, W347, W439, W469, G476, and G477 of the mature polypeptide of SEQ ID NO: 1, wherein each alteration is independently a substitution, deletion or insertion, and wherein the variant has at least 80%, or at least 87%, but less than 100% sequence identity with the mature polypeptide of any of SEQ ID NOs 1, 2, 3, 4, 5, 6, 7, 8, 9, 10, 11 or 12, and wherein the variant has alpha-amylase activity; and a cleaning adjunct, preferably in an amount from 0.01 to 99.9 wt %.

The invention also provides a method of treating a surface, preferably a textile, comprising
(i) forming an aqueous wash liquor comprising water and such a cleaning composition,
(ii) treating the surface with the aqueous wash liquor preferably at a temperature of 40° C. or less, or more preferably at a temperature of 30° C. or less, most preferably at a temperature of 20° C. or less; and
(iii) rinsing the surface.

DETAILED DESCRIPTION OF THE INVENTION

The present invention provides a cleaning composition comprising:
(a) a variant of a parent alpha-amylase, comprising an alteration at two or more (several) positions corresponding to positions G304, W140, W189, D134, E260, F262, W284, W347, W439, W469, G476, and G477 of the mature polypeptide of SEQ ID NO: 1, wherein each alteration is independently a substitution, deletion or insertion, and wherein the variant has at least 80%, or at least 87%, but less than 100% sequence identity with the mature polypeptide of any of SEQ ID NOs 1, 2, 3, 4, 5, 6, 7, 8, 9, 10, 11 or 12, and wherein the variant has alpha-amylase activity; and
(b) a cleaning adjunct, preferably in an amount from 0.01 to 99.9 wt %.

DEFINITIONS

Alpha-amylase activity: The term "alpha-amylase activity" means the activity of alpha-1,4-glucan-4-glucanohydrolases, E.C. 3.2.1.1, which constitute a group of enzymes, which catalyze hydrolysis of starch and other linear and branched 1,4-glucosidic oligo- and polysaccharides.

Variant: The term "variant" means a polypeptide having alpha-amylase activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

Mutant: The term "mutant" means a polynucleotide encoding a variant.

Wild-Type Enzyme: The term "wild-type" alpha-amylase means an alpha-amylase expressed by a naturally occurring microorganism, such as a bacterium, yeast, or filamentous fungus found in nature.

Parent or Parent alpha-amylase: The term "parent" or "parent alpha-amylase" means an alpha-amylase to which an alteration is made to produce the enzyme variants of the present invention. The parent may be a naturally occurring (wild-type) polypeptide or a variant thereof.

Isolated variant: The term "isolated variant" means a variant that is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS-PAGE.

Substantially pure variant: The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc.

Mature polypeptide coding sequence: The term "mature polypeptide coding sequence" means a polynucleotide that encodes a mature polypeptide having alpha-amylase activity.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Fragment: The term "fragment" means a polypeptide having one or more (several) amino acids deleted from the amino and/or carboxyl terminus of a mature polypeptide; wherein the fragment has alpha-amylase activity.

Subsequence: The term "subsequence" means a polynucleotide having one or more (several) nucleotides deleted from the 5'- and/or 3'-end of a mature polypeptide coding sequence; wherein the subsequence encodes a fragment having alpha-amylase activity.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" means a polynucleotide that is modified by the hand of man. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Coding sequence: The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Starch removing process: The expression "starch removing process" relates to any kind of process whereby starch is removed (or converted) such as in washing processes where starch is removed from textile e.g. textile cleaning such as laundry. A starch removing process could also be hard surface cleaning such as dish wash or it could be cleaning processes in general such as industrial or institutional cleaning. The expression also comprises other starch removing processes or starch conversion, ethanol production, starch liquefaction, textile desizing, paper and pulp production, beer making and detergents in general.

Improved property: The term "improved property" means a characteristic associated with a variant that is improved compared to the parent. Such improved properties include, but are not limited to, thermal activity, thermostability, pH activity, pH stability, substrate/cofactor specificity, improved surface properties, product specificity, increased stability or solubility in the presence of pretreated biomass, improved stability under storage conditions, and chemical stability.

Wash performance: In the present context the term "wash performance" is used as an enzyme's ability to remove starch or starch-containing stains present on the object to be cleaned during e.g. laundry or hard surface cleaning, such as dish wash. The wash performance may be quantified by calculating the so-called intensity value (Int) defined in the description of AMSA or in the beaker wash performance test in the Methods section below.

Improved wash performance: The term "improved wash performance" is defined herein as a variant enzyme displaying an alteration of the wash performance of an amylase variant relative to the wash performance of the parent amylase or relative to an alpha-amylase having the identical amino acid sequence of said variant but not having the deletion at one or more of the specified positions or relative to the activity of an alpha-amylase having the amino acid sequence shown in SEQ ID NO 4, e.g. by increased stain removal. The term "wash performance" includes cleaning in general e.g. hard surface cleaning as in dish wash, but also wash performance on textiles such as laundry, and also industrial and institutional cleaning.

Low temperature: "Low temperature" is a temperature of 5-35° C., preferably 5-30° C., more preferably 5-25° C., more preferably 5-20° C., most preferably 5-15° C., and in particular 5-10° C. In a preferred embodiment, "Low temperature" is a temperature of 10-35° C., preferably 10-30° C., more preferably 10-25° C., most preferably 10-20° C., and in particular 10-15° C.

Conventions for Designation of Variants

For purposes of the present invention, the mature polypeptide disclosed in SEQ ID NO: 1 is used to determine the corresponding amino acid residue in another alpha-amylase. The amino acid sequence of another alpha-amylase is aligned with the mature polypeptide disclosed in SEQ ID NO: 1, SEQ ID NO: 2, SEQ ID NO: 3, SEQ ID NO: 4, SEQ ID NO: 5, SEQ ID NO: 6, and based on the alignment, the amino acid position number corresponding to any amino acid residue in the mature polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Identification of the corresponding amino acid residue in another alpha-amylase can be confirmed by an alignment of multiple polypeptide sequences using "ClustalW" (Larkin et al., 2007, *Bioinformatics* 23: 2947-2948).

When the other enzyme has diverged from the mature polypeptide of SEQ ID NO: 2, SEQ ID NO: 2, SEQ ID NO: 3, SEQ ID NO: 4, SEQ ID NO: 5, or SEQ ID NO: 6 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementations of these algorithms can additionally be utilized to query structure databases with a structure of interest in order to discover possible structural homologs (e.g., Holm and Park, 2000, *Bioinformatics* 16: 566-567).

In describing the alpha-amylase variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position*. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G-K-A |

Multiple Alterations.

Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different Substitutions.

Where different substitutions can be introduced at a position, the different substitutions are separated by a comma, e.g., "Arg170Tyr,Glu" represents a substitution of arginine with tyrosine or glutamic acid at position 170. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

Parent Alpha-Amylases

The parent alpha-amylase may be a polypeptide with at least 80% sequence identity with the mature polypeptide of SEQ ID NO: 1.

In an aspect, the parent has a sequence identity to the mature polypeptide of SEQ ID NO: 1 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 1.

The parent preferably comprises or consists of the amino acid sequence of SEQ ID NO: 1. In another aspect, the parent comprises or consists of the mature polypeptide of SEQ ID NO: 1.

In another embodiment, the parent is an allelic variant of the mature polypeptide of SEQ ID NO: 1.

The parent alpha-amylase may also be a polypeptide with at least 80% sequence identity with the mature polypeptide of SEQ ID NO: 2.

In another aspect, the parent has a sequence identity to the mature polypeptide of SEQ ID NO: 2 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 2.

The parent preferably comprises or consists of the amino acid sequence of SEQ ID NO: 2. In another aspect, the parent comprises or consists of the mature polypeptide of SEQ ID NO: 2.

In another embodiment, the parent is an allelic variant of the mature polypeptide of SEQ ID NO: 2.

The parent alpha-amylase may also be a polypeptide with at least 80% sequence identity with the mature polypeptide of SEQ ID NO: 3.

In another aspect, the parent has a sequence identity to the mature polypeptide of SEQ ID NO: 3 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 3.

The parent preferably comprises or consists of the amino acid sequence of SEQ ID NO: 3. In another aspect, the parent comprises or consists of the mature polypeptide of SEQ ID NO: 3.

In another embodiment, the parent is an allelic variant of the mature polypeptide of SEQ ID NO: 3.

The parent alpha-amylase may also be a polypeptide with at least 80% sequence identity with the mature polypeptide of SEQ ID NO: 4.

In another aspect, the parent has a sequence identity to the mature polypeptide of SEQ ID NO: 4 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 4.

The parent preferably comprises or consists of the amino acid sequence of SEQ ID NO: 4. In another aspect, the parent comprises or consists of the mature polypeptide of SEQ ID NO: 4.

In another embodiment, the parent is an allelic variant of the mature polypeptide of SEQ ID NO: 4.

The parent alpha-amylase may also be a polypeptide with at least 80% sequence identity with the mature polypeptide of SEQ ID NO: 5.

In another aspect, the parent has a sequence identity to the mature polypeptide of SEQ ID NO: 5 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 5.

The parent preferably comprises or consists of the amino acid sequence of SEQ ID NO: 5. In another aspect, the parent comprises or consists of the mature polypeptide of SEQ ID NO: 5.

In another embodiment, the parent is an allelic variant of the mature polypeptide of SEQ ID NO: 5.

The parent alpha-amylase may also be a polypeptide with at least 80% sequence identity with the mature polypeptide of SEQ ID NO: 6.

In another aspect, the parent has a sequence identity to the mature polypeptide of SEQ ID NO: 6 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 6.

The parent preferably comprises or consists of the amino acid sequence of SEQ ID NO: 6. In another aspect, the parent comprises or consists of the mature polypeptide of SEQ ID NO: 6.

In another embodiment, the parent is an allelic variant of the mature polypeptide of SEQ ID NO: 6.

The parent alpha-amylase may also be a polypeptide with at least 80% sequence identity with the mature polypeptide of SEQ ID NO: 7.

In another aspect, the parent has a sequence identity to the mature polypeptide of SEQ ID NO: 7 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 7.

The parent preferably comprises or consists of the amino acid sequence of SEQ ID NO: 7. In another aspect, the parent comprises or consists of the mature polypeptide of SEQ ID NO: 7.

In another embodiment, the parent is an allelic variant of the mature polypeptide of SEQ ID NO: 7.

The parent alpha-amylase may also be a polypeptide with at least 80% sequence identity with the mature polypeptide of SEQ ID NO: 8.

In another aspect, the parent has a sequence identity to the mature polypeptide of SEQ ID NO: 8 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 8.

The parent preferably comprises or consists of the amino acid sequence of SEQ ID NO: 8. In another aspect, the parent comprises or consists of the mature polypeptide of SEQ ID NO: 8.

In another embodiment, the parent is an allelic variant of the mature polypeptide of SEQ ID NO: 8.

The parent alpha-amylase may also be a polypeptide with at least 80% sequence identity with the mature polypeptide of SEQ ID NO: 9.

In another aspect, the parent has a sequence identity to the mature polypeptide of SEQ ID NO: 9 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 9.

The parent preferably comprises or consists of the amino acid sequence of SEQ ID NO: 9. In another aspect, the parent comprises or consists of the mature polypeptide of SEQ ID NO: 9.

In another embodiment, the parent is an allelic variant of the mature polypeptide of SEQ ID NO: 9.

The parent alpha-amylase may also be a polypeptide with at least 80% sequence identity with the mature polypeptide of SEQ ID NO: 10.

In another aspect, the parent has a sequence identity to the mature polypeptide of SEQ ID NO: 10 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 10.

The parent preferably comprises or consists of the amino acid sequence of SEQ ID NO: 10. In another aspect, the parent comprises or consists of the mature polypeptide of SEQ ID NO: 10.

In another embodiment, the parent is an allelic variant of the mature polypeptide of SEQ ID NO: 10.

The parent alpha-amylase may also be a polypeptide with at least 80% sequence identity with the mature polypeptide of SEQ ID NO: 11.

In another aspect, the parent has a sequence identity to the mature polypeptide of SEQ ID NO: 11 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 11.

The parent preferably comprises or consists of the amino acid sequence of SEQ ID NO: 11. In another aspect, the parent comprises or consists of the mature polypeptide of SEQ ID NO: 11.

In another embodiment, the parent is an allelic variant of the mature polypeptide of SEQ ID NO: 11.

The parent alpha-amylase may also be a polypeptide with at least 80% sequence identity with the mature polypeptide of SEQ ID NO: 12.

In another aspect, the parent has a sequence identity to the mature polypeptide of SEQ ID NO: 12 of at least 80%, e.g., at least 85%, at least 87%, at least 90%, at least 95%, at least 96%, at least 97%, at least 98%, at least 99%, or 100%, which have alpha-amylase activity. In one aspect, the amino acid sequence of the parent differs by no more than ten amino acids, e.g., by five amino acids, by four amino acids, by three amino acids, by two amino acids, and by one amino acid from the mature polypeptide of SEQ ID NO: 12.

The parent preferably comprises or consists of the amino acid sequence of SEQ ID NO: 12. In another aspect, the parent comprises or consists of the mature polypeptide of SEQ ID NO: 12.

In another embodiment, the parent is an allelic variant of the mature polypeptide of SEQ ID NO: 12.

The amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or a fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material, which is used in a Southern blot.

For purposes of the present invention, hybridization indicates that the polynucleotide hybridizes to a labeled nucleotide probe corresponding to a polynucleotide encoding SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or a subsequence thereof, under low to very high stringency conditions. Molecules to which the probe hybridizes can be detected using, for example, X-ray film or any other detection means known in the art.

In one aspect, the nucleic acid probe is a polynucleotide that encodes the polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or a fragment thereof.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), 50° C. (low stringency), 55° C. (medium stringency), 60° C. (medium-high stringency), 65° C. (high stringency), or 70° C. (very high stringency).

For short probes that are about 15 nucleotides to about 70 nucleotides in length, stringency conditions are defined as prehybridization and hybridization at about 5° C. to about 10° C. below the calculated $T_m$ using the calculation according to Bolton and McCarthy (1962, Proc. Natl. Acad. Sci. USA 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The parent may be obtained from microorganisms of any genus. For purposes of the present invention, the term "obtained from" as used herein in connection with a given source shall mean that the parent encoded by a polynucleotide is produced by the source or by a cell in which the polynucleotide from the source has been inserted. In one aspect, the parent is secreted extracellularly.

The parent may be a bacterial alpha-amylase. For example, the parent may be a gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* alpha-amylase, or a gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* alpha-amylase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* alpha-amylase.

In another aspect, the parent is a *Streptococcus equisimilis, Streptococcus pyogenes, Streptococcus uberis,* or *Streptococcus equi* subsp. *Zooepidemicus* alpha-amylase.

In another aspect, the parent is a *Streptomyces achromogenes, Streptomyces avermitilis, Streptomyces coelicolor, Streptomyces griseus,* or *Streptomyces lividans* alpha-amylase.

The parent may be a fungal alpha-amylase. For example, the parent may be a yeast alpha-amylase such as a *Candida, Kluyveromyces, Pichia, Saccharomyces, Schizosaccharomyces,* or *Yarrowia* alpha-amylase. For example, the parent may be a filamentous fungal alpha-amylase such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* alpha-amylase.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* alpha-amylase.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* alpha-amylase.

In another aspect, the parent is a *Bacillus* sp. alpha-amylase, e.g., the alpha-amylase of SEQ ID NO: 1, SEQ ID NO: 2, SEQ ID NO: 3, SEQ ID NO: 4, SEQ ID NO: 5, or SEQ ID NO: 6.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc,) using the above-mentioned probes.

Techniques for isolating microorganisms and DNA directly from natural habitats are well known in the art. The polynucleotide encoding a parent may then be derived by similarly screening a genomic or cDNA library of another microorganism or mixed DNA sample. Once a polynucleotide encoding a parent has been detected with a probe(s), the polynucleotide may be isolated or cloned by utilizing techniques that are known to those of ordinary skill in the art (see, e.g., Sambrook et al., 1989, supra).

The parent may be a hybrid polypeptide in which a portion of one polypeptide is fused at the N-terminus or the C-terminus of a portion of another polypeptide.

The parent may also be a fused polypeptide or cleavable fusion polypeptide in which one polypeptide is fused at the N-terminus or the C-terminus of another polypeptide. A fused polypeptide is produced by fusing a polynucleotide encoding one polypeptide to a polynucleotide encoding another polypeptide. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Preparation of Variants

The method for obtaining a variant having alpha-amylase activity, may comprise: (a) introducing into a parent alpha-amylase an alteration at two or more (several) positions corresponding to positions 140, 181, 189, 134, 260, 262, 284, 304, 347, 439, 469, 476 and 477 optionally in addition to one or more alterations at positions corresponding to positions 195, 206, 243 of the mature polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, wherein the numbering is according to SEQ ID NO 1 and the variant has alpha-amylase activity; and (b) recovering the variant.

In one aspect a method for obtaining a variant useful in the present invention having alpha-amylase activity, may comprise: (a) introducing into a parent alpha-amylase an alteration at two or more (several) positions corresponding to W140, R181, W189, D134, E260, F262, W284, G304, W347, W439, W469, G476, and G477, optionally in addition to one or more alterations at positions corresponding to positions 195, 206, 243 of the mature polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, wherein the numbering is according to SEQ ID NO 1 and the variant has alpha-amylase activity; and (b) recovering the variant.

In one embodiment the introduced alteration is a substitution.

In yet another embodiment the method for obtaining a variant having alpha-amylase activity, may bcomprise: (a) introducing into a parent alpha-amylase a substitution at two or more (several) positions corresponding to G304RKEQ), W140YF, W189EGT, D134E, E260ADCQLMFPSWVGHIKNRTY, F262GP, W284DHFYR, W347HFY, W439RG, G476EQRK, G477EQKMR of the mature polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, wherein the numbering is according to SEQ ID NO 1 and the variant has alpha-amylase activity; and (b) recovering the variant.

In a preferred embodiment, the introduced substitutions are two or more of G304R, W140YF, W189EGT, D134E, E260GHIKNRTY, W284DFR, W439RG, G476EK, G477EKMR. In a more preferred embodiment, the introduced substitutions are G304R, W140YF, E260GHIKNPRTY and G476EQRK. In an even more preferred embodiment, the method for obtaining a variant having alpha-amylase activity, comprisises: (a) introducing into a parent alpha-amylase substitutions of G304R, W140Y, E260G and G476K in any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, wherein the numbering is according to SEQ ID NO 1 and the variant has alpha-amylase activity; and (b) recovering the variant.

The variants can be prepared using any mutagenesis procedure known in the art, such as site-directed mtagenesis, synthetic gene construction, semi-synthetic gene construction, random mutagenesis, shuffling, etc.

Site-directed mutagenesis is a technique in which one or more (several) mutations are created at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein olgionucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic constuction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR ampflication. Polynucleotide subsequences may then be shuffled.

Variants

The variants of a parent alpha-amylase useful in the present invention comprising an alteration at two or more (several) positions corresponding to positions G304, W140, W189, D134, E260, F262, W284, W347, W439, W469, G476, and G477 of the mature polypeptide of SEQ ID NO: 1, and wherein each alteration is independently a substitution, insertion or deletion (preferably a substitution) and the variant has alpha-amylase activity. Hereby, variants are provided which have improved washing performance at low temperature, compared to the parent alpha-amylase or compared to the alpha-amylase of SEQ ID NO: 1, 2, 3, 4, 5, 6, 7, 8, 9, 10, 11 or 12.

In an embodiment, the variant has sequence identity of at least 85%, at least 87%, at least 90%, at least 95%, at least 96%, at least 97%, at least 98%, or at least 99%, but less than 100%, to the amino acid sequence of the parent alpha-amylase.

Variants useful in the present invention are isolated variants of an alpha-amylase, comprising an alteration at two or more (several) positions corresponding to positions G304, W140, W189, D134, E260, F262, W284, W347, W439, W469, G476, and G477 of the mature polypeptide of SEQ ID NO: 1, wherein each alteration is independently a substitution, deletion or insertion, and wherein the variant has at least 80% but less than 100% sequence identity with the mature polypeptide of any of SEQ ID NOs 1, 2, 3, 4, 5, 6, 7, 8, 9, 10, 11 or 12, and wherein the variant has alpha-amylase activity.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 1.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 2.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 3.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 4.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 5.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 6.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 7.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 8.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 9.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 10.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 11.

In another embodiment, the variant has at least 85%, at least 87%, at least 90%, at least 95%, such as at least 96%, at least 97%, at least 98%, and at least 99%, but less than 100%, sequence identity with the mature polypeptide of SEQ ID NO: 12.

In one aspect, the number of alterations in the variants of the present invention is 1-20, e.g., 1-10 and 1-5, such as 1, 2, 3, 4, 5, 6, 7, 8, 9 or 10 alterations.

In one aspect, a variant comprises an alteration at two or more (several) positions corresponding to positions G304, W140, W189, D134, E260, F262, W284, W347, W439, W469, G476, and G477. In another aspect, a variant comprises an alteration at two positions corresponding to any of positions G304, W140, W189, D134, E260, F262, W284, W347, W439, W469, G476, and G477. In another aspect, a variant comprises an alteration at three positions corresponding to any of positions G304, W140, W189, D134, E260, F262, W284, W347, W439, W469, G476, and G477. In another aspect, a variant comprises an alteration at four positions corresponding to any of positions G304, W140, W189, D134, E260, F262, W284, W347, W439, W469, G476, and G477. In another aspect, a variant comprises an alteration at five positions corresponding to any of positions G304, W140, W189, D134, E260, F262, W284, W347, W439, W469, G476, and G477. In another aspect, a variant comprises an alteration at six positions corresponding to any of positions G304, W140, W189, D134, E260, F262, W284, W347, W439, W469, G476, and G477. In another aspect, a variant comprises an alteration at each position corresponding to positions G304, W140, W189, D134, E260, F262, W284, W347, W439, W469, G476, and G477. The positions correspond to the positions of SEQ ID NO: 1. It is preferred that the alterations are substitutions.

In one embodiment, the variant comprises a substitution at two, three or four positions selected from the group consisting of G304, W140, W189, D134, E260, F262, W284, W347, W439, W469, G476, and G477, optionally also comprising a substitution at one, two or three poisitions selected from the group corresponding to positions N195, V206 and Y243.

In a preferred embodiment, the variant comprises a substitution at two, three or four positions selected from the group consisting of G304, W140, E260 and G476.

In one aspect of the invention, the variant comprises two or more (several) substitutions selected from the group consisting of G304RKEQ, W140YF, W189EGT, D134E, E260ADCQLMFPSWVGHIKNRTY, F262GP, W284DHFYR, W347HFY, W439RG, G476EQRK, G477EQKMR.

It is preferred that the variant according to the invention comprises substitutions at two, three or four positions selected from the group consisting of G304R, W140YF, E260GHIKNPRTY and G476EQRK. In a more preferred embodiment, the substitutions at the two, three or four positions are selected from the group consisting of G304R, W140Y, E260G and G476K.

In one embodiment, the variant further comprises one or more substitutions selected from the group consisting of T51IL, S52Q, N54K, G109A, E194D, N195F, V206Y, Y243F, G109A, G273DV, G337N, K72R, R181H, 5303G and Y100I. In a preferred embodiment the one or more further substitutions are selected from the group consisting of N195F, V206Y, Y243F.

Preferably, the variant comprises two or three of these substitutions. Hereby, variants are provided that have improved wash performance at low temperature as well as improved stability to $Ca^{2+}$ depletion, compared to the parent alpha-amylase or compared to the alpha-amylase of SEQ ID NO: 1, 2, 3, 4, 5, 6, 7, 8, 9, 10, 11 or 12.

In another aspect, the variant useful in the present invention comprises two or more (several) substitutions of the mature polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12, selected from the group consisting of D134E, E260G, E260H, E260I, E260K, E260N, E260R, E260T, G109A, G273D, G273V, G337N, G476E, G477E, G477M, G477R, K72R, R181H, 5303G, W140F, W140Y, W189E, W189G, W189T, W284D, and Y100I.

The variants may further comprise an alteration at one or more (several) other positions. For example, the variants may comprise an alteration at a position corresponding to positions N195F+V206Y+Y243F and/or G182*±D183*or D183*+G184*.

In another aspect, the invention relates to variants which comprise substitutions in the positions, corresponding to the positions of the polypeptide of SEQ ID NO: 1, selected from the group consisting of:
W140Y+N195F+V206Y+Y243F+E260G+G477E,
W140Y+N195F+V206Y+Y243F+E260T+W284D,
W140Y+N195F+V206Y+Y243F+W284D,
G109A+W140Y+N195F+V206Y+Y243F+E260G,
W140Y+N195F+V206Y+Y243F+E260G,
N195F+V206Y+Y243F+E260K+W284D,
D134E+G476E,
W140Y+N195F+V206Y+Y243F+E260G+G476E,
W140Y+W189G+N195F+V206Y+Y243F+E260G,
W140Y+N195F+V206Y+Y243F+E260G+5303G,
W140Y+W189T+N195F+V206Y+Y243F+E260G,
W140Y+N195F+V206Y+Y243F+E260G+W284D,
Y100I+W140Y+N195F+V206Y+Y243F+E260G,
W140Y+N195F+V206Y+Y243F+E260G+G337N,
W140Y+N195F+V206Y+Y243F+E260G+W439R
G109A+W140Y+E194D+N195F+V206Y+Y243F+E260G
G109A+W140Y+N195F+V206Y+Y243F+E260G+G476E
T51I+Y100I+G109A+W140Y+N195F+V206Y+Y243F+E260G
T51I+G109A+W140Y+N195F+V206Y+Y243F+E260G+W439R
T51I+S52Q+N54K+G109A+W140Y+N195F+V206Y+Y243F+E260G+G476E
W140Y+N195F+V206Y+Y243F+E260G+G304R+G476K
W140Y+N195F+V206Y+Y243F+E260G+W284R+G477K
W140Y+N195F+V206Y+Y243F+E260G+W284F+G477R,
and
N195F+V206Y+Y243F+E260G+W284D.

In another aspect, the invention relates to variants which consist of substitutions in the positions, corresponding to the positions of the polypeptide of SEQ ID NO: 1, selected from the group consisting of:
W140Y+N, 195F+V206Y+Y243F+E260G+G477E,
W140Y+N195F+V206Y+Y243F+E260T+W284D,
W140Y+N195F+V206Y+Y243F+W284D,
G109A+W140Y+N195F+V206Y+Y243F+E260G,
W140Y+N195F+V206Y+Y243F+E260G,
N195F+V206Y+Y243F+E260K+W284D,
D134E+G476E,
W140Y+N195F+V206Y+Y243F+E260G+G476E,
W140Y+W189G+N195F+V206Y+Y243F+E260G,
W140Y+N195F+V206Y+Y243F+E260G+5303G,
W140Y+W189T+N195F+V206Y+Y243F+E260G,
W140Y+N195F+V206Y+Y243F+E260G+W284D,
Y100I+W140Y+N195F+V206Y+Y243F+E260G,
W140Y+N195F+V206Y+Y243F+E260G+G337N,
W140Y+N195F+V206Y+Y243F+E260G+W439R
G109A+W140Y+E194D+N195F+V206Y+Y243F+E260G
G109A+W140Y+N195F+V206Y+Y243F+E260G+G476E
T51I+Y100I+G109A+W140Y+N195F+V206Y+Y243F+E260G
T51I+G109A+W140Y+N195F+V206Y+Y243F+E260G+W439R T51I+S52Q+N54K+G109A+W140Y+N195F+V206Y+
  Y243F+E260G+G476E
W140Y+N195F+V206Y+Y243F+E260G+G304R+
  G476K
W140Y+N195F+V206Y+Y243F+E260G+W284R+
  G477K
W140Y+N195F+V206Y+Y243F+E260G+W284F+
  G477R,
and
N195F+V206Y+Y243F+E260G+W284D.

In yet another aspect, the suitable variants comprise alterations in the positions, corresponding to the positions of the polypeptide of SEQ ID NO: 1, selected from the group consisting of:
D183*+G184*±W140Y+N195F+V206Y+Y243F+
  E260G+G477E,
D183*+G184*±W140Y+N195F+V206Y+Y243F+
  E260T+W284D,
D183*+G184*±W140Y+N195F+V206Y+Y243F+
  W284D,
D183*+G184*±G109A+W140Y+N195F+V206Y+
  Y243F+E260G,
D183*+G184*+W140Y+N195F+V206Y+Y243F+
  E260G,
D183*+G184*+N195F+V206Y+Y243F+E260K+
  W284D,
D183*+G184*+D134E+G476E,
D183*+G184*+W140Y+N195F+V206Y+Y243F+
  E260G+G476E,
D183*+G184*+W140Y+W189G+N195F+V206Y+
  Y243F+E260G,
D183*+G184*+W140Y+N195F+V206Y+Y243F+
  E260G+S303G,
D183*+G184*+W140Y+W189T+N195F+V206Y+
  Y243F+E260G,
D183*+G184*+W140Y+N195F+V206Y+Y243F+
  E260G+W284D,
D183*+G184*+Y100I+W140Y+N195F+V206Y+
  Y243F+E260G,
D183*+G184*+W140Y+N195F+V206Y+Y243F+
  E260G+G337N,
D183*+G184*+W140Y+N195F+V206Y+Y243F+
  E260G+W439R
D183*+G184*+G109A+W140Y+E194D+N195F+
  V206Y+Y243F+E260G
D183*+G184*+G109A+W140Y+N195F+V206Y+
  Y243F+E260G+G476E
D183*+G184*+T51I+Y100I+G109A+W140Y+N195F+
  V206Y+Y243F+E260G
D183*+G184*+T51I+G109A+W140Y+N195F+
  V206Y+Y243F+E260G+W439R
D183*+G184*+T51I+S52Q+N54K+G109A+W140Y+
  N195F+V206Y+Y243F+E260G+G476E
D183*+G184*+W140Y+N195F+V206Y+Y243F+
  E260G+G304R+G476K
D183*+G184*+W140Y+N195F+V206Y+Y243F+
  E260G+W284R+G477K
D183*+G184*+W140Y+N195F+V206Y+Y243F+
  E260G+W284F+G477R, and
D183*+G184*+N195F+V206Y+Y243F+E260G+
  W284D.

In another aspect, the suitable variants consist of alterations in the positions, corresponding to the positions of the polypeptide of SEQ ID NO: 1, selected from the group consisting of:
D183*+G184*±W140Y+N195F+V206Y+Y243F+
  E260G+G477E,
D183*+G184*±W140Y+N195F+V206Y+Y243F+
  E260T+W284D,
D183*+G184*±W140Y+N195F+V206Y+Y243F+
  W284D,
D183*+G184*±G109A+W140Y+N195F+V206Y+
  Y243F+E260G,
D183*+G184*+W140Y+N195F+V206Y+Y243F+
  E260G,
D183*+G184*+N195F+V206Y+Y243F+E260K+
  W284D,
D183*+G184*+D134E+G476E,
D183*+G184*+W140Y+N195F+V206Y+Y243F+
  E260G+G476E,
D183*+G184*+W140Y+W189G+N195F+V206Y+
  Y243F+E260G,
D183*+G184*+W140Y+N195F+V206Y+Y243F+
  E260G+S303G,
D183*+G184*+W140Y+W189T+N195F+V206Y+
  Y243F+E260G,
D183*+G184*+W140Y+N195F+V206Y+Y243F+
  E260G+W284D,
D183*+G184*+Y100I+W140Y+N195F+V206Y+
  Y243F+E260G,
D183*+G184*+W140Y+N195F+V206Y+Y243F+
  E260G+G337N,
D183*+G184*+W140Y+N195F+V206Y+Y243F+
  E260G+W439R
D183*+G184*+G109A+W140Y+E194D+N195F+
  V206Y+Y243F+E260G
D183*+G184*+G109A+W140Y+N195F+V206Y+
  Y243F+E260G+G476E
D183*+G184*+T51I+Y100I+G109A+W140Y+N195F+
  V206Y+Y243F+E260G
D183*+G184*+T51I+G109A+W140Y+N195F+
  V206Y+Y243F+E260G+W439R
D183*+G184*+T51I+S52Q+N54K+G109A+W140Y+
  N195F+V206Y+Y243F+E260G+G476E
D183*+G184*+W140Y+N195F+V206Y+Y243F+
  E260G+G304R+G476K
D183*+G184*+W140Y+N195F+V206Y+Y243F+
  E260G+W284R+G477K
D183*+G184*+W140Y+N195F+V206Y+Y243F+
  E260G+W284F+G477R,
and
D183*+G184*+N195F+V206Y+Y243F+E260G+
  W284D.

Essential amino acids in a parent can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the alpha-amylase or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent.

Compositions

The present invention also relates to compositions comprising a variant of the present invention. Preferably, the compositions are enriched in such a variant. The term "enriched" means that the alpha-amylase activity of the composition has been increased, e.g., with an enrichment factor of 1.1.

The composition may comprise a variant as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger*, or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarchochroum, Fusarium sulphureum, Fusarium toruloseum, Fusarium trichothecioides*, or *Fusarium venenatum; Humicola*, e.g., *Humicola insolens* or *Humicola lanuginosa*; or *Trichoderma*, e.g., *Trichoderma harzianum, Trichoderma koningii, Trichoderma longibrachiatum, Trichoderma reesei*, or *Trichoderma viride*.

The compositions may be prepared in accordance with methods known in the art and may be in the form of a liquid or a dry composition. For instance, the composition may be in the form of a granulate or a microgranulate. The variant may be stabilized in accordance with methods known in the art.

Cleaning Compositions

The present invention preferably relates to products for and/or methods relating to and/or use of the claimed compositions that are for air care, car care, dishwashing, fabric conditioning (including softening), laundry detergency, laundry and rinse additive and/or care, hard surface cleaning and/or treatment, and other cleaning for consumer or institutional use. According to the invention, the above alpha-amylase variants may typically be a component in a cleaning composition, such as a solid, liquid, gel and/or unit dose detergent composition, e.g., a laundry detergent composition or a dishwashing detergent composition. Especially preferred is a liquid laundry detergent composition.

Such cleaning compositions comprise a cleaning/detergent adjunct, preferably a mixture of components. Typically the cleaning adjunct will be present in the composition in an amount from 0.001 to 99.9 wt %, more typically from 0.01 to 80 wt % cleaning adjunct. Suitable cleaning adjuncts comprise: surfactants, builders, bleaches, bleach catalysts, colorants, bleach boosters, chelating agents, dye transfer agents, deposition aids, dispersants, additional enzymes, and enzyme stabilizers, catalytic materials, bleach activators, hydrogen peroxide, sources of hydrogen peroxide, optical brighteners, photoactivators, fluorescers, fabric hueing agents, fabric conditioners, preformed peracids, polymeric dispersing agents, clay soil removal/anti-redeposition agents, filler salts, hydrotropes, brighteners, suds suppressors, structure elasticizing agents, fabric softeners, hydrolyzable surfactants, preservatives, anti-oxidants, anti-shrinkage agents, germicides, fungicides, anti-tarnish, anti-corrosion agents, alkalinity sources, solubilizing agents, carriers, processing aids, pigments, dyes, perfumes and pH control agents, encapsulates, polymers. For example, these may include: bleach ingredients such as imine bleach boosters; sources of hydrogen peroxide such as percarbonate and/or perborate, especially percarbonate coated with material such as carbonate and/or sulphate salt, silicate salt, borosilicate, and any mixture thereof; pre-formed peracid, including pre-formed peracid in encapsulated form; transition metal catalysts; suds suppressors or suppressor systems such as silicone based suds suppressors and/or fatty acid based suds suppressors; fabric-softeners such as clay, silicone and/or quaternary ammonium compounds; flocculants such as polyethylene oxide; dye transfer inhibitors such as polyvinylpyrrolidone, poly 4-vinylpyridine N-oxide and/or co-polymer of vinylpyrrolidone and vinylimidazole; fabric integrity components such as oligomers produced by the condensation of imidazole and epichlorhydrin; soil dispersants and soil anti-redeposition aids such as alkoxylated polyamines and ethoxylated ethyleneimine polymers; anti-redeposition components such as polyesters; carboxylate polymers such as maleic acid polymers or co-polymers of maleic and acrylic acid; perfumes such as perfume microcapsules, starch encapsulated accords, perfume spray-on; soap rings; aesthetic particles; dyes; fillers such as sodium sulphate, although it is preferred for the composition to be substantially free of fillers; silicate salt such as sodium silicate, including 1.6R and 2.0R sodium silicate, or sodium metasilicate; co-polyesters of di-carboxylic acids and diols; cellulosic polymers such as methyl cellulose, carboxymethyl cellulose, hydroxyethoxycellulose, or other alkyl or alkylalkoxy cellulose; solvents such as 1,2 propanediol, monoethanolamine; diethylene glycol, ethanol, and any mixture thereof; hydrotropes such as sodium cumene sulphonate, sodium xylene sulphonate, sodium toluene sulphonate, and any mixtures; organic acids such as citric acid; and any combination thereof.

In another preferred aspect the composition comprises one or more surfactants, which may be non-ionic including semi-polar and/or anionic and/or cationic and/or zwitterionic and/or ampholytic and/or semi-polar nonionic and/or mixtures thereof. The surfactants are typically present at a level of from 0.1% to 60% by weight or from 0.5 to 50 wt % or 1 to 40 wt % of the composition.

When included therein the cleaning composition will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the cleaning agent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The cleaning composition may comprise one or more other enzymes such as a protease, a lipase, a peroxidase, another amylolytic enzyme, e.g., another alpha-amylase, glucoamylase, maltogenic amylase, CGTase and/or a cellulase, mannanase (such as MANNAWAY™ from Novozymes, Denmark), pectinase, pectate lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include metalloproteases and/or serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from Bacillus, such as Bacillus lentus, B. alkalophilus, B. subtilis, B. amyloliquefaciens, Bacillus pumilus and Bacillus gibsonii described in U.S. Pat. No. 6,312,936 B1, U.S. Pat. No. 5,679,630, U.S. Pat. No. 4,760,025, US 7,262,042 and WO09/021867.

(b) trypsin-type or chymotrypsin-type proteases, such as trypsin (e.g., of porcine or bovine origin), including the Fusarium protease described in WO 89/06270 and the chymotrypsin proteases derived from Cellumonas described in WO 05/052161 and WO 05/052146.

(c) metalloproteases, including those derived from Bacillus amyloliquefaciens described in WO 07/044993A2.

Preferred proteases include those derived from Bacillus gibsonii or Bacillus Lentus.

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Properase®, Purafect®, Purafect Prime®, Purafect Ox®, FN3®, FN4®, Excellase® and Purafect OXP® by Genencor International, those sold under the tradename Opticlean® and Optimase® by Solvay Enzymes, those available from Henkel/Kemira, namely BLAP (sequence shown in FIG. 29 of U.S. Pat. No. 5,352,604 with the following mutations S99D+S101R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)—all from Henkel/Kemira; and KAP (Bacillus alkalophilus subtilisin with mutations A230V+S256G+S259N) from Kao. Further suitable proteases are described in WO2011/03623, WO2011/140316, WO2011/140364 and WO2012/05778.

Lipases: Suitable lipases include those of bacterial or fungal origin. Chemically modified or protein engineered mutants are included. Examples of useful lipases include lipases from Humicola (synonym Thermomyces), e.g., from H. lanuginosa p(T. lanuginosus) as described in EP 258 068 and EP 305 216 or from H. insolens as described in WO 96/13580, a Pseudomonas lipase, e.g., from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g., from B. subtilis (Dartois et al. (1993), Biochemica et Biophysica Acta, 1131, 253-360), B. stearothermophilus (JP 64/744992) or B. pumilus (WO 91/16422).

The lipase may be a "first cycle lipase" such as those described in U.S. Pat. No. 6,939,702 B1 and US PA 2009/0217464. In one aspect, the lipase is a first-wash lipase, preferably a variant of the wild-type lipase from Thermomyces lanuginosus comprising T231R and N233R mutations. The wild-type sequence is the 269 amino acids (amino acids 23-291) of the Swissprot accession number Swiss-Prot 059952 (derived from Thermomyces lanuginosus (Humicola lanuginosa)). Preferred lipases would include those sold under the tradenames Lipex®, Lipolex® and Lipoclean®.

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. No. 4,435,307, U.S. Pat. No. 5,648,263, U.S. Pat. No. 5,691,178, U.S. Pat. No. 5,776,757, WO09/148983, U.S. Pat. No. 7,141,403B2 and WO 89/09259.

In one aspect, preferred enzymes include microbial-derived endoglucanases exhibiting endo-beta-1,4-glucanase activity (E.C. 3.2.1.4), prefrebaly selected from the group comprising:

(a) a bacterial polypeptide endogenous to a member of the genus Bacillus which has a sequence of at least 90%, 94%, 97% and even 99% identity to the amino acid sequence SEQ ID NO:2 in U.S. Pat. No. 7,141,403B2;

(b) a glycosyl hydrolase having enzymatic activity towards both xyloglucan and amorphous cellulose substrates, wherein the glycosyl hydrolase is selected from GH families 5, 12, 44 or 74;

(c) a glycosyl hydrolase having a sequence of at least 90%, 94%, 97% and even 99% identity to the amino acid sequence SEQ ID NO:3 in WO09/148983;

(d) and mixtures thereof.

Suitable endoglucanases are sold under the tradenames Celluclean® and Whitezyme® (Novozymes A/S, Bagsvaerd, Denmark).

Other commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases: Suitable peroxidases/oxidases include those of plant, bac-terial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257.

Commercially available peroxidases include GUARDZYME® (Novozymes A/S).

Other enzymes: Other preferred enzymes include pectate lyases sold under the tradenames Pectawash®, Pectaway® and mannanases sold under the tradenames Mannaway® (all from Novozymes A/S, Bagsvaerd, Denmark), and Purabrite® (Genencor International Inc., Palo Alto, Calif.).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Direct, Basic, Reactive or hydrolysed Reactive, Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes such as those described in EP1794275 or EP1794276, or dyes as disclosed in U.S. Pat. No. 7,208,459 B2, and mixtures thereof. In another aspect, suitable small molecule dyes include small molecule dyes selected from the group consisting of Colour Index numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in WO2011/98355, WO2011/47987, US2012/090102, WO2010/145887, WO2006/055787 and WO2010/142503.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Preferred hueing dyes include the whitening agents found in WO 08/87497 A1, WO2011/011799 and WO2012/054835. Preferred hueing agents for use in the present invention may be the preferred dyes disclosed in these references, including those selected from Examples 1-42 in Table 5 of WO2011/011799. Other preferred dyes are disclosed in U.S. Pat. No. 8,138,222.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of Ultramarine Blue (C.I. Pigment Blue 29), Ultramarine Violet (C.I. Pigment Violet 15) and mixtures thereof. Builders—The cleaning composition may further contain builders, such as builders based on carbonate, bicarbonate or silicates which may be Zeolites, such as Zeolite A, Zeolite MAP (Maximum Aluminium type P). Zeolites, useable in laundry preferably has the formula $Na_{12}(AlO_2)_{12}(SiO_2)_{12}.27H_2O$ and the particle size is usually between 1-10 μm for zeolite A and 0.7-2 um for zeolite MAP. Other builders are Sodium metasilicate ($Na_2SiO_3.nH_2O$ or $Na_2Si_2O_5.n\ H_2O$) strong alkaline and preferably used in dish wash. In preferred embodiments, the amount of a detergent builder may be above 5%, above 10%, above 20%, above 30%, above 40% or above 50%, and may be below 80%, 65%. In a dishwash detergent, the level of builder is typically 40-65%, particularly 50-65% or even 75-90%.

Encapsulates—The composition may comprise an encapsulate. In one aspect, an encapsulate comprising a core, a shell having an inner and outer surface, said shell encapsulating said core.

In one aspect of said encapsulate, said core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

In one aspect of said encapsulate, said core may comprise perfume. Such encapsulates are perfume microcapsules.

In one aspect of said encapsulate, said shell may comprise melamine formaldehyde and/or cross linked melamine formaldehyde.

In a one aspect, suitable encapsulates may comprise a core material and a shell, said shell at least partially surrounding said core material, is disclosed. At least 75%, 85% or even 90% of said encapsulates may have a fracture strength of from about 0.2 MPa to about 10 MPa, from about 0.4 MPa to about SMPa, from about 0.6 MPa to about 3.5 MPa, or even from about 0.7 MPa to about 3 MPa; and a benefit agent leakage of from 0% to about 30%, from 0% to about 20%, or even from 0% to about 5%.

In one aspect, at least 75%, 85% or even 90% of said encapsulates may have a particle size of from about 1 microns to about 80 microns, about 5 microns to 60 microns, from about 10 microns to about 50 microns, or even from about 15 microns to about 40 microns.

In one aspect, at least 75%, 85% or even 90% of said encapsulates may have a particle wall thickness of from about 30 nm to about 250 nm, from about 80 nm to about 180 nm, or even from about 100 nm to about 160 nm.

In one aspect, said encapsulates' core material may comprise a material selected from the group consisting of a perfume raw material and/or optionally a material selected from the group consisting of vegetable oil, including neat and/or blended vegetable oils including caster oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil and mixtures thereof; aromatic solvents, including benzene, toluene and mixtures thereof; silicone oils; and mixtures thereof.

In one aspect, said encapsulates' wall material may comprise a suitable resin including the reaction product of an aldehyde and an amine, suitable aldehydes include, formaldehyde. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof.

In one aspect, suitable formaldehyde scavengers may be employed with the encapsulates, for example, in a capsule slurry and/or added to a consumer product before, during or after the encapsulates are added to such consumer product.

Suitable capsules that can be made by following the teaching of USPA 2008/0305982 A1; and/or USPA 2009/0247449 A1. Alternatively, suitable capsules can be purchased from Appleton Papers Inc. of Appleton, Wis. USA.

In addition, the materials for making the aforementioned encapsulates can be obtained from Solutia Inc. (St Louis, Miss. U.S.A.), Cytec Industries (West Paterson, N.J. U.S.A.), sigma-Aldrich (St. Louis, Miss. U.S.A.), CP Kelco Corp. of San Diego, Calif., USA; BASF AG of Ludwigshafen, Germany; Rhodia Corp. of Cranbury, N.J., USA; Hercules Corp. of Wilmington, Del., USA; Agrium Inc. of Calgary, Alberta, Canada, ISP of New Jersey U.S.A., Akzo Nobel of Chicago, Ill., USA; Stroever Shellac Bremen of Bremen, Germany; Dow Chemical Company of Midland, Mich., USA; Bayer AG of Leverkusen, Germany; Sigma-Aldrich Corp., St. Louis, Miss., USA.

In one aspect, the composition may comprise an enzyme stabilizer selected from the group consisting of (a) inorganic salts selected from the group consisting of calcium salts, magnesium salts and mixtures thereof; (b) carbohydrates selected from the group consisting of oligosaccharides, polysaccharides and mixtures thereof; (c) mass efficient reversible protease inhibitors selected from the group consisting of phenyl boronic acid and derivatives thereof; and (d) mixtures thereof.

In another embodiment, the composition comprises: (1) reversible protease inhibitors such as a boron containing compound; (2) 1-2 propane diol; (3) calcium formate and/or sodium formate; and (4) any combination thereof.

In one aspect, the composition may comprise a structurant selected from the group consisting of diglycerides and triglycerides, ethylene glycol distearate microcrystalline cellulose, cellulose-based materials, microfiber cellulose, biopolymers, xanthan gum, gellan gum, and mixtures thereof.

Polymers

The consumer product may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers and amphiphilic polymers.

Amphiphilic Cleaning Polymers

Preferably, the amphiphilic cleaning polymer is a compound having the following general structure: bis(($C_2H_5O$)($C_2H_4O$)n)($CH_3$)—$N^+$—$C_xH_{2x}$—$N^+$($CH_3$)-bis(($C_2H_5O$)($C_2H_4O$)n), wherein n=from 20 to 30, and x=from 3 to 8, or sulphated or sulphonated variants thereof.

Amphiphilic alkoxylated grease cleaning polymers of the present invention refer to any alkoxylated polymer having balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure. These may comprise alkoxylated polyalkylenimines, preferably having an inner polyethylene oxide block and an outer polypropylene oxide block.

The core structure may comprise a polyalkylenimine structure comprising, in condensed form, repeating units of formulae (I), (II), (III) and (IV):

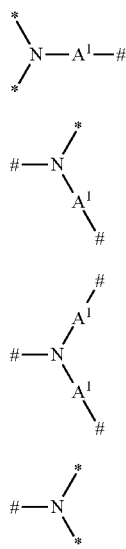

wherein # in each case denotes one-half of a bond between a nitrogen atom and the free binding position of a group $A^1$ of two adjacent repeating units of formulae (I), (II), (III) or (IV); * in each case denotes one-half of a bond to one of the alkoxylate groups; and $A^1$ is independently selected from linear or branched $C_2$-$C_6$-alkylene; wherein the polyalkylenimine structure consists of 1 repeating unit of formula (I), x repeating units of formula (II), y repeating units of formula (III) and y+1 repeating units of formula (IV), wherein x and y in each case have a value in the range of from 0 to about 150; where the average weight average molecular weight, Mw, of the polyalkylenimine core structure is a value in the range of from about 60 to about 10,000 g/mol.

The core structure may alternatively comprise a polyalkanolamine structure of the condensation products of at least one compound selected from N-(hydroxyalkyl)amines of formulae (I.a) and/or (I.b),

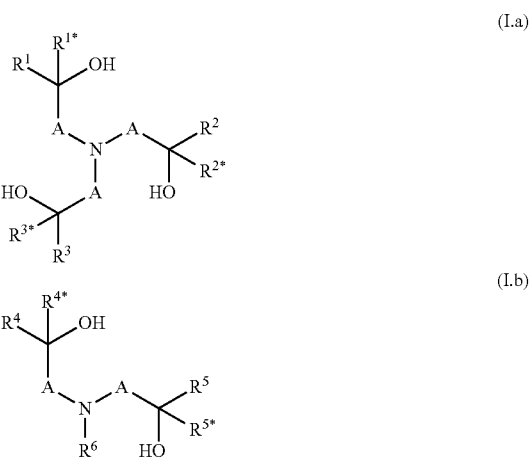

wherein A are independently selected from $C_1$-$C_6$-alkylene; $R^1$, $R^{1*}$, $R^2$, $R^{2*}$, $R^3$, $R^{3*}$, $R^4$, $R^{4*}$, $R^5$ and $R^{5*}$ are independently selected from hydrogen, alkyl, cycloalkyl or aryl, wherein the last three mentioned radicals may be optionally substituted; and $R^6$ is selected from hydrogen, alkyl, cycloalkyl or aryl, wherein the last three mentioned radicals may be optionally substituted.

The plurality of alkylenoxy groups attached to the core structure are independently selected from alkylenoxy units of the formula (V)

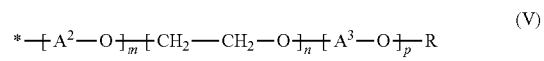

wherein * in each case denotes one-half of a bond to the nitrogen atom of the repeating unit of formula (I), (II) or (IV); $A^2$ is in each case independently selected from 1,2-propylene, 1,2-butylene and 1,2-isobutylene; $A^3$ is 1,2-propylene; R is in each case independently selected from hydrogen and $C_1$-$C_4$-alkyl; m has an average value in the range of from 0 to about 2; n has an average value in the range of from about 20 to about 50; and p has an average value in the range of from about 10 to about 50.

Specific embodiments of the amphiphilic alkoxylated grease cleaning polymers may be selected from alkoxylated polyalkylenimines having an inner polyethylene oxide block and an outer polypropylene oxide block, the degree of ethoxylation and the degree of propoxylation not going above or below specific limiting values. Specific embodiments of the alkoxylated polyalkylenimines according to the present invention have a minimum ratio of polyethylene blocks to polypropylene blocks (n/p) of about 0.6 and a maximum of about $1.5(x+2y+1)^{1/2}$. Alkoxykated polyalkyenimines having an n/p ratio of from about 0.8 to about $1.2(x+2y+1)^{1/2}$ have been found to have especially beneficial properties.

The alkoxylated polyalkylenimines according to the present invention have a backbone which consists of primary, secondary and tertiary amine nitrogen atoms which are attached to one another by alkylene radicals A and are randomly arranged. Primary amino moieties which start or terminate the main chain and the side chains of the polyalkylenimine backbone and whose remaining hydrogen atoms are subsequently replaced by alkylenoxy units are referred to as repeating units of formulae (I) or (IV), respectively. Secondary amino moieties whose remaining hydrogen atom is subsequently replaced by alkylenoxy units are referred to as repeating units of formula (II). Tertiary amino moieties which branch the main chain and the side chains are referred to as repeating units of formula (III).

Since cyclization can occur in the formation of the polyalkylenimine backbone, it is also possible for cyclic amino moieties to be present to a small extent in the backbone. Such polyalkylenimines containing cyclic amino moieties are of course alkoxylated in the same way as those consisting of the noncyclic primary and secondary amino moieties.

The polyalkylenimine backbone consisting of the nitrogen atoms and the groups $A^1$, has an average molecular weight Mw of from about 60 to about 10,000 g/mole, preferably from about 100 to about 8,000 g/mole and more preferably from about 500 to about 6,000 g/mole.

The sum (x+2y+1) corresponds to the total number of alkylenimine units present in one individual polyalkylenimine backbone and thus is directly related to the molecular weight of the polyalkylenimine backbone. The values given in the specification however relate to the number average of all polyalkylenimines present in the mixture. The sum (x+2y+2) corresponds to the total number amino groups present in one individual polyalkylenimine backbone.

The radicals $A^1$ connecting the amino nitrogen atoms may be identical or different, linear or branched $C_2$-$C_6$-alkylene radicals, such as 1,2-ethylene, 1,2-propylene, 1,2-butylene, 1,2-isobutylene,1,2-pentanediyl, 1,2-hexanediyl or hexamethylen. A preferred branched alkylene is 1,2-propylene. Preferred linear alkylene are ethylene and hexamethylene. A more preferred alkylene is 1,2-ethylene.

The hydrogen atoms of the primary and secondary amino groups of the polyalkylenimine backbone are replaced by alkylenoxy units of the formula (V).

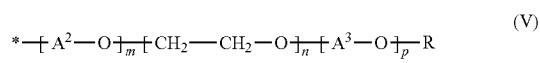

(V)

In this formula, the variables preferably have one of the meanings given below:

$A^2$ in each case is selected from 1,2-propylene, 1,2-butylene and 1,2-isobutylene; preferably $A^2$ is 1,2-propylene. $A^3$ is 1,2-propylene; R in each case is selected from hydrogen and $C_1$-$C_4$-alkyl, such as methyl, ethyl, n-propyl, isopropyl, n-butyl, isobutyl and tert.-butyl; preferably R is hydrogen. The index m in each case has a value of 0 to about 2; preferably m is 0 or approximately 1; more preferably m is 0. The index n has an average value in the range of from about 20 to about 50, preferably in the range of from about 22 to about 40, and more preferably in the range of from about 24 to about 30. The index p has an average value in the range of from about 10 to about 50, preferably in the range of from about 11 to about 40, and more preferably in the range of from about 12 to about 30.

Preferably the alkylenoxy unit of formula (V) is a non-random sequence of alkoxylate blocks. By non-random sequence it is meant that the $[-A^2-O-]_m$ is added first (i.e., closest to the bond to the nitrgen atom of the repeating unit of formula (I), (II), or (III)), the $[-CH_2-CH_2-O-]_n$ is added second, and the $[-A^3-O-]_p$ is added third. This orientation provides the alkoxylated polyalkylenimine with an inner polyethylene oxide block and an outer polypropylene oxide block.

The substantial part of these alkylenoxy units of formula (V) is formed by the ethylenoxy units $-[CH_2-CH_2-O)]-$ and the propylenoxy units $-[CH_2-CH_2(CH_3)-O]_p-$. The alkylenoxy units may additionally also have a small proportion of propylenoxy or butylenoxy units $-[A^2-O]_m-$, i.e. the polyalkylenimine backbone saturated with hydrogen atoms may be reacted initially with small amounts of up to about 2 mol, especially from about 0.5 to about 1.5 mol, in particular from about 0.8 to about 1.2 mol, of propylene oxide or butylene oxide per mole of NH-moieties present, i.e. incipiently alkoxylated.

This initial modification of the polyalkylenimine backbone allows, if necessary, the viscosity of the reaction mixture in the alkoxylation to be lowered. However, the modification generally does not influence the performance properties of the alkoxylated polyalkylenimine and therefore does not constitute a preferred measure.

The amphiphilic alkoxylated grease cleaning polymers are present in the fabric and home care products, including but not limited to detergents, of the present invention at levels ranging from about 0.05% to 10% by weight of the fabric and home care product. Embodiments of the fabric and home care products may comprise from about 0.1% to about 5% by weight. More specifically, the embodiments may comprise from about 0.25 to about 2.5% of the grease cleaning polymer.

Carboxylate polymer—The consumer products of the present invention may also include one or more carboxylate polymers such as a maleate/acrylate random copolymer or polyacrylate homopolymer. In one aspect, the carboxylate polymer is a polyacrylate homopolymer having a molecular weight of from 4,000 Da to 9,000 Da, or from 6,000 Da to 9,000 Da.

Soil release polymer—The consumer products of the present invention may also include one or more soil release polymers having a structure as defined by one of the following structures (I), (II) or (III):

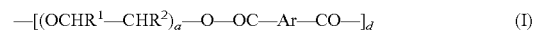 (I)

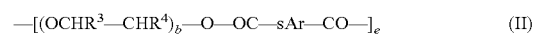 (II)

 (III)

wherein:

a, b and c are from 1 to 200;

d, e and f are from 1 to 50;

Ar is a 1,4-substituted phenylene;

sAr is 1,3-substituted phenylene substituted in position 5 with $SO_3Me$;

Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;

$R^1$, $R^2$, $R^3$, $R^4$, $R^5$ and $R^6$ are independently selected from H or $C_1$-$C_{18}$ n- or iso-alkyl; and $R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

Cellulosic polymer—The consumer products of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 Da to 300,000 Da.

The detergent may contain a bleaching system, which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type. In general, when a bleaching agent is used, the compositions of the present invention may comprise from about 0.1% to about 50% or even from about 0.1% to about 25% bleaching agent by weight of the subject cleaning composition.

Chelating Agents—The consumer products herein may contain a chelating agent. Suitable chelating agents include copper, iron and/or manganese chelating agents and mixtures thereof. When a chelating agent is used, the subject consumer product may comprise from about 0.005% to about 15% or even from about 3.0% to about 10% chelating agent by weight of the subject consumer product. Suitable chelants include DTPA (Diethylene triamine pentaacetic acid), HEDP (Hydroxyethane diphosphonic acid), DTPMP (Diethylene triamine penta(methylene phosphonic acid)), 1,2-Dihydroxybenzene-3,5-disulfonic acid disodium salt hydrate, ethylenediamine, diethylene triamine, ethylenediaminedisuccinic acid (EDDS), N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof.

The enzyme variants of the invention may be stabilized using conventional stabilizing agents, and/or protease inhibitors e.g., a polyol such as propylene glycol or glycerol, a sugar or sugar alcohol, salts such as sodium chloride and potassium chloride, lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2x(X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO09118375, WO98/13459) or a protease inhibitor of the protein type such as RASI, BASI, WASI (bifunctional alpha-amylase/subtilisin inhibitors of rice, barley and wheat) or CI2 or SSI. The composition may be formulated as described in, e.g., WO 92/19709 and WO 92/19708 or U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

The composition may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, organic solvents such as ethanol or perfumes. Furthermore, the detergent could contain a pre-spotter or a booster, which is added to the wash to increase the general cleaning level, some of these additives may also be used as a pre-treatment agent applied to the textile before the washing step.

It is at present contemplated that in the detergent compositions any enzyme, in particular the enzyme of the invention, may be added in an amount corresponding to 0.001-100 mg of enzyme protein per liter of wash liquor, preferably 0.005-5 mg of enzyme protein per liter of wash liquor, more preferably 0.01-1 mg of enzyme protein per liter of wash liquor and in particular 0.1-1 mg of enzyme protein per liter of wash liquor. However, the compositions of the present invention comprise at least 0.0001 to about 0.1% weight percent of pure enzyme protein, such as from about 0.0001% to about 0.01%, from about 0.001% to about 0.01% or from about 0.001% to about 0.01%. However, when using a formulated enzyme the detergent composition comprises from about 0.02% to about 20% weight percent, such as or from about 0.05% to about 15% weight, or from about 0.05 to about 20%, or from about 0.05% to about 5%, or from about 0.05% to about 3%.

The alpha-amylase variants useful in the present invention may additionally be incorporated in the detergent formulations disclosed in WO 97/07202, which is hereby incorporated as reference.

The detergent composition of the invention may be in any convenient form, e.g., a bar, a tablet, a powder, a granule, a paste, a gel or a liquid. The composition may be a powder-form all-purpose "heavy-duty" washing agent, a paste-form all-purpose, a heavy-duty liquid type, a liquid fine-fabric, a hand dishwashing agent, a light duty dishwashing agent, a high-foaming type. a machine dishwashing agent, a various tablet, a dishwash granular, a dish wash liquid, a rinse-aid type. The composition can also be in unit dose packages, including those known in the art and those that are water soluble, water insoluble and/or water permeable. A liquid detergent may be aqueous, typically containing up to 70% water and 0-30% organic solvent, or non-aqueous or a solution containing more than 0.5 g/L of the detergent composition.

The composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. The detergent may be a powder, or granulated form, or it may be in the form of a liquid, gel or paste or in the form of a unit dose product such as a tablet or pouch, including multi-compartment pouches, or the detergent can be in the form of a sheet.

EXAMPLES pNP-G7 Assay for Determination of Alpha-Amylase Activity

The alpha-amylase activity may be determined by a method employing the G7-pNP substrate. G7-pNP which is an abbreviation for 4,6-ethylidene($G_7$)-p-nitrophenyl($G_1$)-α, D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm.). Kits containing G7-pNP substrate and alpha-Glucosidase is manufactured by Roche/Hitachi (cat. No. 11876473).
Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether ($C_{14}H_{22}O(C_2H_4O)_n$ (n=9-10))), 1 mM CaCl2, pH8.0.
Procedure:

The amylase sample to be analyzed was diluted in dilution buffer to ensure the pH in the diluted sample is 7. The assay was performed by transferring 20 µl diluted enzyme samples to 96 well microtiter plate and adding 80 µl substrate working solution. The solution was mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Automatic Mechanical Stress Assay (AMSA) for Laundry

In order to assess the wash performance in laundry washing experiments are performed, using the Automatic Mechanical Stress Assay (AMSA). With the AMSA, the wash performance of a large quantity of small volume enzyme-detergent solutions can be examined The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner For further description see WO02/42740 especially the paragraph "Special method embodiments" at page 23-24.
General Wash Performance Description A test solution comprising water (10° dH), detergent, e.g. 5.1 g/L European liquid detergent as described below and the enzyme of the invention, e.g. at concentration of 0, 0.8 and/or 1.2 mg enzyme protein/L, is prepared. Fabrics stained with starch (e.g. CS-28 from Center For Testmaterials BV, P.O. Box 120, 3133 KT, Vlaardingen, The Netherlands) is added and washed for 20 minutes at 20° C. After thorough rinse under running tap water and drying in the dark, the light intensity or reflectance values of the stained fabrics are subsequently measured as a measure for wash performance. The test with 0 mg enzyme protein/L is used as a blank to obtain a delta remission value. Preferably mechanical action is applied during the wash step, e.g. in the form of shaking, rotating or stirring the wash solution with the fabrics.

The AMSA wash performance experiments were conducted under the experimental conditions specified below:

TABLE 1

| AMSA experimental conditions | |
| --- | --- |
| Laundry liquid detergent dosage | 5.7 g/L European (EU) liquid detergent, or 0.8 g/L Northern America (US) liquid detergent |
| Test solution volume | 160 micro L |
| pH | as is |
| Wash time | 20 minutes |
| Temperature | 20° C. |
| Water hardness | 10°dH, $Ca^{2+}$:$Mg^{2+}$:$HCO_3^-$ = 3:1:6 |
| Enzyme concentration in test solution | 0.8-1.2 Mg/L |
| Test material | CS-28 (Rice starch on cotton) |

Amylase dilution buffer: Amylase was diluted in ultrapure water (MilliQ water) with a small concentration of calcium (0.1 mM) to stabilize the amylase during storage and 0.01% Triton X-100 to reduce risk of adsorption of enzyme protein to containers and pipettes.

Water hardness was adjusted to 10° dH by addition of $CaCl_2$, $MgCl_2$, and $NaHCO_3$ ($Ca^{2+}$:$Mg^{2+}$: $HCO_3^-$=3:1:4.5) to the test system. After washing the textiles were flushed in tap water and dried.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore the intensity of the reflected light can be used to measure wash performance.

Color measurements are made with a professional flatbed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}.$$

Textiles: Textile sample CS-28 (rice starch on cotton) is obtained from Center For Testmaterials BV, P.O. Box 120, 3133 KT Vlaardingen, the Netherlands.

Results of the AMSA laundry test of different variants are shown in Table 3. In the result the index is 100. The performance result of the parent alpha-amylase is assigned the value of 100 and the results of the variants are compared to this value.

AMSA Wash Performance

The wash performance of the variants and corresponding parent alpha-amylases were tested by the AMSA-test method as described in the Methods section. The results are given as (performance of variant minus performance of blank) divided by (performance of parent minus performance of blank) multiplied by 100, where the blank is the performance obtained by washing at the same conditions, but in the absence of alpha-amylase. Finally a mean of relative performance at the two concentrations 0.8-1.2 Mg/L were calculated.
Results are presented in Table 3.

Terg-O-tometer (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment:

The water bath with 12 steel beakers and 1 rotating arm per beaker with capacity of 500 or 1200 mL of detergent solution. Temperature ranges from 5 to 80° C. The water bath has to be filled up with deionised water. Rotational speed can be set up to 70 to 120 rpm/min TOM Wash Performance Water hardness was adjusted to the strength described below by addition of $CaCl_2$, $MgCl_2$ and $NAHCO_3$. Wash solutions were prepared with desired amount of detergent, temperature and water hardness in a bucket as described below. Detergent was dissolved during magnet stirring for 10 min (Wash solution was used within 30 to 60 min after preparation).

Temperature and rotation (rpm) in the water bath in the Terg-O-Tometer were set according to the settings below. When temperature was adjusted according to settings (tolerance is +/−0.5° C.) wash solution was added to TOM beaker according to the amount described below.

Agitation in the beaker was at 120 rpm. 2 rice starch swatches (CS-28) and soil ballast were added to each of the beakers and wash carried out according to time stated below. The swatches were rinsed in cold tap water for 5 min. The swatches were left to dry in the dark over night.

Textile: Textile sample CS-28 (rice starch on cotton) was obtained from Center for Testmaterials BV, P.O. Box 120, 3133 KT Vlaardingen, the Netherlands.

Soil ballast: Soil ballast Rice starch on cotton/polyester (EMPA 162) was obtained from Center for Testmaterials BV, P.O. Box 120, 3133 KT Vlaardingen, the Netherlands. Bistro gravy (063KC), Frij Chocolate milkshake, Heinz spaghetti (113KC), Herseys double chocolate was obtained from Warwick Equest Ltd, Unit 55, Consett Business Park, Consett, County Durham, DH8 6BN UK Results of the TOM wash test of different variants are shown in Table 3. In the result the index is 100. The performance result of the parent alpha-amylase (SEQ ID NO:7) is assigned the value of 100 and the results of the variants are compared to this value.

TABLE 2

| Experimental conditions | | |
|---|---|---|
| | European (EU) conditions | Northern America (US) conditions |
| Detergent dosage | 5.77 g/L (liquid detergent) | 0.78 g/L (liquid detergent) |
| Water hardness | 15°dH ($Ca^{2+}:Mg^{2+}:HCO_3^-$ = 4:1:7.5) | 6°dH ($Ca^{2+}:Mg^{2+}:HCO_3^-$ = 2:1:4.5) |
| Enzyme concentration in wash solution | 0.25 mg ep/L | 0.08 mg ep/L |
| Test solution volume | 500 ml | 800 ml |
| Wash time | 30 minutes | 18 minutes |
| Rotation | 120 rpm | |
| pH | as is | |
| Temperature | 15° C. | |

Detergents and test materials were as follows:

| | |
|---|---|
| Laundry liquid detergent | European (EU) conditions: Regular HDL (heavy duty liquid) as described in Example 1A below. Northern American (US) conditions: Regular HDL (heavy duty liquid) as described in Example 1B below. |
| Test material | CS-28 (Rice starch on cotton) |
| Soil ballast | Rice starch on polyester/cotton (EMPA 162), Bistro gravy (063KC), Frij Chocolate milkshake, Heinz spaghetti (113KC), Herseys double chocolate (2 swatches of each) |

The wash performance was measured as the brightness of the colour of the textile washed expressed in remission values. Remission measurements were made using a Macbeth 7000 Color Eye spectrophotometer. Each of the dry swatches was measured. As there is a risk of interference from the back-ground, the swatches were placed on top of 4 layers of fabric during the measurement of the remission. The remission was measured at 460 nm. The UV filter was not included. An average result for remission for the swatches was calculated.

Example 1

Wash Performance of Alpha-Amylases in European (EU) (Example 1A) and Northern American (Example 1B) (US) Liquid Detergent The wash performance of the tested variant and corresponding parent alpha-amylase (SEQ ID NO: 7) were tested as described above. The results are given as (performance of variant minus performance of blank) divided by (performance of parent minus performance of blank) multiplied by 100; where the blank is the performance obtained by washing at the same conditions, but in the absence of alpha-amylase.

Example 1A

European Heavy Duty Liquid Laundry Detergent Composition

| Example 1A | (wt %) |
|---|---|
| Sodium Alkylbenzene sulfonate | 11.7 |
| Citric acid | 2.27 |

-continued

| Example 1A | (wt %) |
|---|---|
| $C_{12-18}$ fatty acid | 0.82 |
| Sodium alkyl ethoxy 3 sulfate | 3.9 |
| $C_{12-18}$ alkyl 1.5-7-ethoxylate | 2.4 |
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulphated or sulphonated variants thereof | 0.66 |
| Random graft co-polymer[1] | 0.83 |
| Phosphonated chelant | 0.48 |
| Brightener | 0.091 |
| Hydrotrope | 0.95 |
| Minors: dyes, perfumes, enzymes, enzyme stabilizers, solvents, structurants. pH modifying agents | Balance |

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

Example 1B: North American Heavy Duty Liquid Laundry Detergent Composition

| Example 1B | (wt %) |
|---|---|
| Sodium Alkyl ethoxy 1.8 sulfate | 17.29 |
| Sodium Alkylbenzene sulfonate | 7.73 |
| Branched alkyl sulfate | 3.3 |
| $C_{12-18}$ Alkyl 1.5-9ethoxylate | 1.31 |
| $C_{12}$ dimethylamine oxide | 1.03 |
| Citric acid | 0.67 |
| $C_{12-18}$ fatty acid | 1.52 |
| Sodium Borate (Borax) | 2.53 |
| Ethoxylated Polyethylenimine [2] | 1.44 |
| Phosphonated chelant | 0.34 |
| Dihydroxybenzene-3,5-disulfonic acid disodium salt hydrate | 0.19 |
| Brightener | 0.29 |
| Amphiphilic alkoxylated grease cleaningpolymer [3] | 1.93 |
| Minors: dyes, perfumes enzymes, enzyme stabilizers, solvents, structurants, pH modifying agents | Balance |

[2] Polyethylenimine (MW = 600) with 20 ethoxylate groups per —NH.
[3] Amphiphilic alkoxylated polymer is a polyethylenimine (MW 600), prepared from a polymer that is derivatised to contain 24 ethoxylate groups per —NH and 16 Propoxylate groups per —NH.

TABLE 3

Wash performance

| Substitutions of SEQ ID NO: 7 (numbering according to SEQ ID NO: 1) | US 20° C. AMSA | US 15° C. TOM | EU 20° C. AMSA | EU 15° C. TOM |
|---|---|---|---|---|
| N195F + V206Y + Y243F | 85 | 113 | 94 | 100 |
| E260I | 99 | 115 | 103 | 126 |
| E260K | 108 | 107 | 119 | 125 |
| W140Y + N195F + V206Y + Y243F | 104 | 108 | 110 | 104 |
| N195F + V206Y + Y243F + W284D | 120 | 107 | 78 | 126 |
| W140F + R181H | 113 | 130 | 122 | 115 |
| N195F + V206Y + E260R + G273D | 94 | 104 | 104 | 95 |
| N195F + V206Y + Y243F + E260K + G273D | 102 | 137 | 91 | 125 |
| D134E + G476E | 120 | 137 | 108 | 120 |
| K72R + N195F + V206Y + Y243F + E260H + G273V | 120 | 132 | 118 | 152 |
| N195F + V206Y + Y243F + E260N + G273V | 97 | 123 | 107 | 102 |
| W140Y + N195F + V206Y + Y243F + E260G | 107 | 149 | 119 | 111 |
| N195F + V206Y + Y243F + E260K + W284D | 136 | 209 | 107 | 116 |
| W140Y + N195F + V206Y + Y243F + E260G + W284D | 144 | 111 | 107 | 101 |
| W140Y + N195F + V206Y + Y243F + E260T + W284D | 138 | 273 | 117 | 120 |
| W189E + N195F + V206Y + Y243F | 108 | 129 | 128 | 117 |
| W140Y + N195F + V206Y + Y243F + W284D | 147 | 254 | 112 | 123 |
| N195F + V206Y + Y243F + G477R | 110 | 108 | 110 | 123 |
| N195F + V206Y + Y243F + G477M | 105 | 110 | 105 | 104 |
| W140Y + W189G + N195F + V206Y + Y243F + E260G | 124 | 132 | 103 | 113 |
| W140Y + N195F + V206Y + Y243F + E260G + G477E | 122 | 313 | 113 | 103 |
| W140Y + N195F + V206Y + Y243F + E260G + G476E | 125 | 114 | 117 | 108 |
| W140Y + N195F + V206Y + Y243F + E260G + S303G | 113 | 112 | 114 | 110 |
| W140Y + W189T + N195F + V206Y + Y243F + E260G | 119 | 112 | 123 | 111 |
| W140Y + N195F + V206Y + Y243F + E260G + G337N | 110 | 109 | 119 | 113 |
| Y100I + W140Y + N195F + V206Y + Y243F + E260G | 128 | 110 | 140 | 109 |
| G109A + W140Y + N195F + V206Y + Y243F + E260G | 115 | 245 | 129 | 116 |
| W140Y + N195F + V206Y + Y243F + E260G + W439R | 124 | 160 | 142 | 125 |
| G109A + W140Y + E194D + N195F + V206Y + Y243F + E260G | 108 | 222 | 117 | 123 |
| G109A + W140Y + N195F + V206Y + Y243F + E260G + G476E | 126 | 188 | 125 | 122 |
| T51I + Y100I + G109A + W140Y + N195F + V206Y + Y243F + E260G | 113 | 175 | 128 | 110 |
| T51I + G109A + W140Y + N195F + V206Y + Y243F + E260G + W439R | 119 | 147 | 127 | 125 |
| T51I + S52Q + N54K + G109A + W140Y + N195F + V206Y + Y243F + E260G + G476E | 129 | 259 | 126 | 113 |
| W140Y + N195F + V206Y + Y243F + E260G + G304R + G476K | 124 | 179 | 135 | 125 |
| W140Y + N195F + V206Y + 243F + E260G + W284R + G477K | 132 | 309 | 144 | 124 |
| W140Y + N195F + V206Y + Y243F + E260G + W284F + G477R | 134 | 298 | 140 | 116 |
| N195F + V206Y + Y243F + E260G + W284D | 115 | 102 | 101 | 107 |
| N195F + V206Y + Y243F + S473T + G476R | 101 | 95 | 113 | 100 |
| N195F + V206Y + Y243F + G476E | 100 | 118 | 100 | 94 |

The wash performance test results clearly demonstrate that the performances of the variants are improved relative to their respective parent molecule (SEQ ID NO 7) at the tested temperatures.

Example 2

Full Scale Washing Machine Performance Evaluation of Amylase Variants in Liquid Detergent I. Preparation of the Detergent Test Compositions In this experiment four test compositions were prepared based on liquid detergent Formulation 2A. A detergent base was prepared from Formulation 2A, containing no enzymes and finished to pH 8.2.

Example 20

Heavy Duty Liquid Laundry Detergent Composition

| Formulation 2A | (wt %) |
|---|---|
| Sodium Alkylbenzene sulfonate | 10.2 |
| Citric acid | 3.14 |
| $C_{12-18}$ fatty acid | 2.59 |
| Sodium Alkyl ethoxy 3 sulfate | 1.17 |
| $C_{12-18}$ Alkyl 1.5-7-ethoxylate | 6.32 |
| A compound having the following general structure: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = from 20 to 30, and x = from 3 to 8, or sulphated or sulphonated variants thereof | 0.63 |
| Random graft co-polymer[1] | 1.07 |
| Phosphonated chelant | 0.41 |
| Brightener | 0.09 |
| Hydrotrope | 0.93 |
| Minors: dyes, perfumes enzymes, enzyme stabilizers, solvents, structurants, pH modifying agents | Balance |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

The following seven detergent formulations were prepared:

| Detergent Formulation 2A | |
|---|---|
| Comparative example A | Nil enzyme |
| Comparative example B | Addition of *0.23 ppm [1]Natalase ® |
| Example C according to the invention | Addition of *0.23 ppm [2]Variant 3 Amylase of this invention |
| Example D according to the invention | Addition of *0.23 ppm [3]Variant 4 Amylase of this invention |
| Example E according to the invention | Addition of *0.23 ppm [4]Variant 5 Amylase of this invention |
| Example F according to the invention | Addition of *0.23 ppm [5]Variant 6 Amylase of this invention |
| Example G according to the invention | Addition of *0.23 ppm [6]Variant 7 Amylase of this invention |

*Added as active enzyme protein

[1]Natalase ® is amylase enzyme supplied by Novozymes A/S, Bagsvaerd, Denmark as 'Natalase 200L'.
[2]Variant 3 is an amylase variant of this invention of the wild-type amylase Bacillus sp722 SEQ ID NO 1 with the following two deletions D183* + G184* and including substitutions G109A, W140Y, N195F, V206Y, Y243F, E260G and G476E. Also referred to as SP722 + D183* + G184* + G109A + W140Y + N195F + V206Y + Y243F + E260G + G476E.
[3]Variant 4 is an amylase variant of this invention of the wild-type amylase Bacillus sp722 SEQ ID NO 1 with the following two deletions D183* + G184* and including substitutions T51I, G109A, W140Y, N195F, V206Y, Y243F, E260G and W439R. Also referred to as SP722 + D183* + G184* + T51I + G109A + W140Y + N195F + V206Y + Y243F + E260G + W439R.
[4]Variant 5 is an amylase variant of this invention of the wild-type amylase Bacillus sp722 SEQ ID NO 1 with the following two deletions D183* + G184* and including substitutions T51I, S52Q, N54K, G109A, W140Y, N195F, V206Y, Y243F, E260G and G476E. Also referred to as SP722 + D183* + G184* + T51I + S52Q + N54K + G109A + W140Y + N195F + V206Y + Y243F + E260G + G476E.
[5]Variant 6 is an amylase variant of this invention of the wild-type amylase Bacillus sp722 SEQ ID NO 1 with the following two deletions D183* + G184* and including substitutions W140Y, N195F, V206Y, Y243F, E260G, G304R and G476K. Also referred to as SP722 + D183* + G184* + W140Y + N195F + V206Y + Y243F + E260G + G304R + G476K.
[6]Variant 7 is an amylase variant of this invention of the wild-type amylase Bacillus sp722 SEQ ID NO 1 with the following two deletions D183* + G184* and including substitutions W140Y, N195F, V206Y, Y243F, E260G, W284R and G477K. Also referred to as SP722 + D183* + G184* + W140Y + N195F + V206Y + Y243F + E260G + W284R + G477K.

II. Test Fabrics

Three amylase sensitive stains; PCS-28 Rice Starch, CS-128 Aged Rice Starch and CS-26 Corn Starch, 5 cm×5 cm (supplied by Centre For Test materials, Netherlands) were attached to 20 cm×20 cm white knitted cotton (supplied by Warwick Equest, Durham, United Kingdom). Two amylase sensitive stains; Chilli Con Carne and Heinz Spaghetti, 2.5 cm in diameter were attached to 20 cm×20 cm white knitted cotton (supplied by Warwick Equest, Durham, United Kingdom). Eight replicates (2 replicates across 4 different machines) were used for each test formulation.

| | |
|---|---|
| Test material | PCS-28 Rice Starch, CS-128 Aged Rice Starch, CS-26 Corn Starch, Chilli Con Carne and Heinz Spaghetti. |
| Soil ballast | Apple and Pear Rice Pudding, Grandma's Sunday Lunch, Tomato Soup, Spaghetti Bolognese Sauce, Sweet and Sour Sauce, Carrot and Potato Babyfood, Bisto Gravy, ASDA Gravy, ASDA Pasta Sauce, BBQ Sauce, Curry Sauce, Frijj Chocolate Milkshake, Leek and Potato Soup, Hershey's Chocolate Syrup (all supplied by Warwick Equest, Durham, United Kingdom). CS-28 Rice Starch, PS-28 Rice Starch, CS-29 Tapioca Starch (all supplied by Centre For Testmaterials, Netherlands). |
| Clean Ballast | 2.5 kg 50:50 mix cotton towels and sheets |

III. Test Wash Procedure

The method involves the use of Western Europe Hotpoint washing machines, model Aquarius WF541. Test formulations as described above were used to wash amylase sensitive stains with the addition of a mixed soil and clean ballast load as described above.

Washing machines containing 6 g/L of test formulation, 13 L water at 10° clark hardness, plus test fabrics & ballast were washed at 15° C. on a fast cotton wash cycle lasting 1 hour and 15 minutes.

After the wash, the test fabrics were line dried indoors. The wash process was repeated for a further 3 wash cycles.

The stain removal index (SRI) (as measured by comparing unwashed to washed L* a* b* values) was then measured in order to quantify the stain removal performance of the detergent compositions.

The performance index was also measured by calculating (performance of Example C, D, E, F or G minus the performance of comparative example A) divided by (performance of comparative example B minus the performance of comparative example A) multiplied by 100.

IV. Comparison of the Samples.

TABLE 1

Average SRI across 5 stains (8 replicates of each stain)

| Example | Average SRI (%) (associated LSD) | Average SRI versus A | Average SRI versus B |
|---|---|---|---|
| Comparative example A | 33.2 (3.7) | — | — |
| Comparative example B | 55.2 (3.7) | 22.0 | — |
| Example C According to the invention | 66.1 (3.7) | 32.9 | 10.9 |
| Example D According to the invention | 64.0 (3.7) | 30.8 | 8.8 |
| Example E According to the invention | 66.8 (3.7) | 33.6 | 11.6 |
| Example F According to the invention | 64.6 (3.7) | 31.4 | 9.4 |
| Example G According to the invention | 67.8 (3.7) | 34.6 | 12.6 |

TABLE 2

Performance Index for Chilli Con Carne (8 replicates)

| Example | Performance Index |
|---|---|
| Comparative example A | — |
| Comparative example B | 100 |
| Example C According to the invention | 169 |
| Example D According to the invention | 145 |
| Example E According to the invention | 181 |
| Example F According to the invention | 178 |
| Example G According to the invention | 188 |

By comparing the samples washed with the composition of example A (nil enzyme present) with example B (containing Natalase), C, D, E, F & G (containing variants 3, 4, 5, 6 & 7 respectively), it is apparent that the stain removal performance is improved by the addition of an amylase enzyme. By comparing the samples washed with the composition of example B (containing Natalase) with examples C, D, E, F & G (containing variants 3, 4, 5, 6 & 7 respectively) according to example A as the reference (nil enzyme), it is apparent that variants 3, 4, 5, 6 & 7 of the invention are able to achieve significantly higher levels of stain removal than Natalase®.

Example 3

Full Scale Washing Machine Performance Evaluation of Amylase Variants in Liquid Detergent I. Preparation of the Detergent Test Compositions In this experiment four test compositions were prepared based on liquid detergent Formulation 3A. A detergent base was prepared from Formulation 3A, containing no enzymes and finished to pH 8.2.

Formulation 3
A Heavy Duty Liquid Laundry Detergent Composition

| Formulation 3A | (wt %) |
|---|---|
| Sodium Alkyl ethoxy 1.8 sulfate | 14.81 |
| Sodium Alkylbenzene sulfonate | 3.53 |
| Branched alkyl sulfate | 2.44 |
| $C_{12-18}$ Alkyl-1.5-9-ethoxylate | 0.88 |
| $C_{12}$ dimethylamine oxide | 0.56 |
| Citric acid | 2.05 |
| $C_{12-18}$ fatty acid | 1.48 |
| Ethoxylated Polyethylenimine [2] | 1.51 |
| Phosphonated chelant | 0.53 |
| Brightener | 0.19 |
| Amphiphilic alkoxylated polymer [3] | 1.25 |
| Minors: dyes, perfumes enzymes, enzyme stabilizers, solvents, structurants, pH modifying agents | Balance |

[2] Polyethylenimine (MW = 600) with 20 ethoxylate groups per —NH.
[3] Amphiphilic alkoxylated polymer is a polyethylenimine (MW 600), prepared from a polymer that is derivatised to contain 24 ethoxylate groups per —NH and 16 Propoxylate groups per —NH.

The following six formulations were prepared:

| Formulation 3A | |
|---|---|
| Comparative example A | Nil enzyme |
| Comparative example B | Addition of *0.1 ppm [1]Natalase ® |
| Example C according to the invention | Addition of *0.1 ppm [2]Variant 5 Amylase of this invention |
| Example D according to the invention | Addition of *0.1 ppm [3]Variant 6 Amylase of this invention |
| Example E according to the invention | Addition of *0.1 ppm [4]Variant 7 Amylase of this invention |
| Example F according to the invention | Addition of *0.1 ppm [5]Variant 8 Amylase of this invention |

*Added as active enzyme protein
[1]Natalase ® is supplied by Novozymes A/S, Bagsvaerd, Denmark as 'Natalase 200L'.
[2]Variant 5 is an amylase variant of this invention of the wild-type amylase Bacillus sp722 SEQ ID NO 1 with the following two deletions D183* + G184* and including substitutions T51I, S52Q, N54K, G109A, W140Y, N195F, V206Y, Y243F, E260G and G476E. Also referred to as SP722 + D183* + G184* + T51I + S52Q + N54K + G109A + W140Y + N195F + V206Y + Y243F + E260G + G476E.
[3]Variant 6 is an amylase variant of this invention of the wild-type amylase Bacillus sp722 SEQ ID NO 1 with the following two deletions D183* + G184* and including substitutions W140Y, N195F, V206Y, Y243F, E260G, G304R and G476K. Also referred to as SP722 + D183* + G184* + W140Y + N195F + V206Y + Y243F + E260G + G304R + G476K.
[4]Variant 7 is an amylase variant of this invention of the wild-type amylase Bacillus sp722 SEQ ID NO 1 with the following two deletions D183* + G184* and including substitutions W140Y, N195F, V206Y, Y243F, E260G, W284R and G477K. Also referred to as SP722 + D183* + G184* + W140Y + N195F + V206Y + Y243F + E260G + W284R + G477K.
[5]Variant 8 is an amylase variant of this invention of the wild-type amylase Bacillus sp722 SEQ ID NO 1 with the following two deletions D183* + G184* and including substitutions W140Y, N195F, V206Y, Y243F, E260G, W284F and G477R. Also referred to as SP722 + D183* + G184* + W140Y + N195F + V206Y + Y243F + E260G + W284F + G477R.

II. Test Fabrics

Three amylase sensitive stains; PCS-28 Rice Starch, PS-28 Rice Starch and CS-29 Tapioca Starch, 5 cm×5 cm (supplied by Centre For Test materials, Netherlands) were attached to 20 cm×20 cm white knitted cotton (supplied by Warwick Equest, Durham, United Kingdom). One amylase sensitive stain; Heinz Spaghetti, 2.5 cm in diameter was attached to 20 cm×20 cm white knitted cotton (supplied by Warwick Equest, Durham, United Kingdom). One amylase sensitive stain; Gravy, 2.5 cm in diameter was attached to 25 cm×24 cm white knitted cotton (supplied by Accurate Product Development, Fairfield, Ohio, USA). Eight replicates (2 replicates across 4 different machines) were used for each test formulation.

| Test materials | PCS-28 Rice Starch, PS-28 Rice Starch, CS-29 Tapioca Starch, Heinz Spaghetti and Gravy. |
|---|---|
| Soil ballast | BBQ Sauce, Bisto Gravy, Chocolate Pudding Babyfood, Hershey's Chocolate Sauce, Tomato Soup, Chilli Con Carne, Spaghetti Bolognese Sauce (all supplied by Warwick Equest, Durham, United Kingdom). Grape Juice, Mustard, Coffee, Blueberry, BBQ Sauce, Blood, Grass, Burnt Butter, Bacon Grease, Double Chocolate Syrup, US Clay, Make Up, Wine, |

Tea and Spaghetti (all supplied by APD, Fairfield, Ohio, United States). CS-28 Rice Starch, CS-128 Aged Rice Starch, CS-26 Corn Starch (all supplied by Centre For Testmaterials, Netherlands).

Clean Ballast 6 x cotton T shirts, 6 x cotton pillowcases, 6 x hand towels

III. Test Wash Procedure

The method involves the use of a North American Kenmore washing machine model 600 series.

Test formulations as described above were used to wash amylase sensitive stains with the addition of a mixed soil and clean ballast load as described above.

Washing machines containing 0.78 g/L test formulation, 64 L water 6° clark water hardness, plus test fabrics & ballast were washed at 15° C. on a 12 minute superwash with one rinse. After the wash, the test fabrics were line dried indoors. The wash process was repeated for a further 3 wash cycles.

The stain removal index (as measured by comparing unwashed to washed L* a* b* values) was then measured in order to quantify the stain removal performance of the detergent compositions.

The performance index was also measured by calculating (performance of Example C, D, E or F minus the performance of comparative example A) divided by (performance of comparative example B minus the performance of comparative example A) multiplied by 100.

IV. Comparison of the Samples.

TABLE 1

Average SRI across 5 stains (8 replicates of each stain)

| Example | Average SRI (%) (associated LSD) | Average SRI versus A | Average SRI versus B |
|---|---|---|---|
| Comparative Example A | 39.5 (4.8) | — | — |
| Comparative Example B | 51.4 (4.8) | 11.9 | — |
| Example C According to the invention | 69.4 (4.8) | 29.9 | 18.0 |
| Example D According to the invention | 64.7 (4.8) | 25.2 | 13.3 |
| Example E According to the invention | 71.3 (4.8) | 31.8 | 19.9 |
| Example F According to the invention | 69.2 (4.8) | 29.7 | 17.8 |

TABLE 2

Performance Index for Heinz Spaghetti (8 replicates)

| Example | Performance Index |
|---|---|
| Comparative Example A | — |
| Comparative Example B | 100 |
| Example C According to the invention | 266 |
| Example D According to the invention | 256 |
| Example E According to the invention | 284 |
| Example F According to the invention | 416 |

By comparing the samples washed with the composition of example A (nil enzyme present) with example B (containing Natalase), C, D, E and F (containing variant 5, 6, 7 and 8 respectively), it is apparent that the stain removal performance is improved by the addition of an amylase enzyme.

By comparing the samples washed with the composition of example B (containing Natalase) with examples C, D, E and F (containing variant 5, 6, 7 and 8 respectively) according to example A as the reference (nil enzyme), it is apparent that variants 5, 6, 7 and 8 of the invention are able to achieve significantly higher levels of stain removal than Natalase®.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Method of Use

The present invention includes a method for cleaning and/or treating a situs inter alia a surface or fabric. In one aspect, such method comprises the steps of optionally washing and/or rinsing said surface or fabric, contacting said surface or fabric with any consumer product disclosed in this specification then optionally washing and/or rinsing said surface or fabric is disclosed.

As used herein, washing includes but is not limited to, scrubbing, and mechanical agitation. Drying of such surfaces or fabrics may be accomplished by any one of the common means employed either in domestic or industrial settings. Such means include but are not limited to forced air or still air drying at ambient or elevated temperatures at pressures between 5 and 0.01 atmospheres in the presence or absence of electromagnetic radiation, including sunlight, infrared, ultraviolet and microwave irradiation. In one aspect, said drying may be accomplished at temperatures above ambient by employing an iron wherein, for example, said fabric may be in direct contact with said iron for relatively short or even extended periods of time and wherein pressure may be exerted beyond that otherwise normally present due to gravitational force. In another aspect, said drying may be accomplished at temperatures above ambient by employing a dryer. Apparatus for drying fabric is well known and it is frequently referred to as a clothes dryer. In addition to clothes such appliances are used to dry many other items including towels, sheets, pillowcases, diapers and so forth and such equipment has been accepted as a standard convenience in many nations of the world substantially replacing the use of clothes lines for drying of fabric. Most dryers in use today use heated air which is passed over and or through the fabric as it is tumbled within the dryer. The air may be heated, for example, either electronically, via gas flame, or even with microwave radiation. Such air may be heated from about 15° C. to about 400° C., from about 25° C. to about 200° C., from about 35° C. to about 100° C., or even from about 40° C. to about 85° C. and used in the dryer to dry a surface and/or a fabric. As will be appreciated by one skilled in the art, the cleaning compositions of the present invention are ideally suited for use in laundry applications. Accordingly, the present invention includes a method for laundering a fabric. The method comprises the steps of contacting a fabric to be laundered with a said cleaning laundry solution comprising at least one embodiment of Applicants' cleaning composition, cleaning additive or mixture thereof. The fabric may comprise most any fabric capable of being laundered in normal consumer or institutional use conditions. The solution preferably has a pH of from about 8 to about 10.5. The compositions may be employed at concentrations of from about 500 ppm to about 15,000 ppm in solution. The water temperatures typically range from about 5° C. to about 90° C. The water to fabric ratio is typically from about 1:1 to about 30:1.

DETERGENT EXAMPLES

Examples 1-6

Granular laundry detergent compositions designed for hand washing or top-loading washing machines.

| | 1 (wt %) | 2 (wt %) | 3 (wt %) | 4 (wt %) | 5 (wt %) | 6 (wt %) |
|---|---|---|---|---|---|---|
| Linear alkylbenzenesulfonate | 20 | 22 | 20 | 15 | 20 | 20 |
| $C_{12-14}$ Dimethylhydroxyethyl ammonium chloride | 0.7 | 0.2 | 1 | 0.6 | 0.0 | 0 |
| AE3S | 0.9 | 1 | 0.9 | 0.0 | 0.5 | 0.9 |
| AE7 | 0.0 | 0.0 | 0.0 | 1 | 0.0 | 3 |
| Sodium tripolyphosphate | 5 | 0.0 | 4 | 9 | 2 | 0.0 |
| Zeolite A | 0.0 | 1 | 0.0 | 1 | 4 | 1 |
| 1.6R Silicate ($SiO_2$:$Na_2O$ at ratio 1.6:1) | 7 | 5 | 2 | 3 | 3 | 5 |
| Sodium carbonate | 25 | 20 | 25 | 17 | 18 | 19 |
| Polyacrylate MW 4500 | 1 | 0.6 | 1 | 1 | 1.5 | 1 |
| Random graft copolymer[1] | 0.1 | 0.2 | 0.0 | 0.0 | 0.0 | 0.0 |
| Carboxymethyl cellulose | 1 | 0.3 | 1 | 1 | 1 | 1 |
| Protease (Savinase ®, 32.89 mg active/g) | 0.1 | 0.1 | 0.1 | 0.1 | | 0.1 |
| Lipase-Lipex ® (18 mg active/g) | 0.03 | 0.07 | 0.3 | 0.1 | 0.07 | 0.4 |
| *Amylase of the present invention (mg active) | 0.63 | 1.0 | 2.0 | 0.44 | 0.88 | 0.3 |
| Fluorescent Brightener 1 | 0.06 | 0.0 | 0.06 | 0.18 | 0.06 | 0.06 |
| Fluorescent Brightener 2 | 0.1 | 0.06 | 0.1 | 0.0 | 0.1 | 0.1 |
| DTPA | 0.6 | 0.8 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.1 | 0.0 | 0.0 | 0.0 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Sulphonated zinc phthalocyanine | 0.0030 | 0.0 | 0.0012 | 0.0030 | 0.0021 | 0.0 |
| S-ACMC | 0.1 | 0.0 | 0.0 | 0.0 | 0.06 | 0.0 |
| Direct Violet 9 | 0.0 | 0.0 | 0.0003 | 0.0005 | 0.0003 | 0.0 |
| Acid Blue 29 | 0.0 | 0.0 | 0.0 | 0.0 | 0.0 | 0.0003 |
| Sulfate/Moisture | | | Balance | | | |

*Amylase of the present invention is shown as mgs of active enzyme per 100 g of detergent.

Examples 7-12

Granular laundry detergent compositions designed for front-loading automatic washing machines.

| | 7 (wt %) | 8 (wt %) | 9 (wt %) | 10 (wt %) | 11 (wt %) | 12 (wt %) |
|---|---|---|---|---|---|---|
| Linear alkylbenzenesulfonate | 8 | 7.1 | 7 | 6.5 | 7.5 | 7.5 |
| AE3S | 0 | 4.8 | 0 | 5.2 | 4 | 4 |
| C12-14 Alkylsulfate | 1 | 0 | 1 | 0 | 0 | 0 |
| AE7 | 2.2 | 0 | 3.2 | 0 | 0 | 0 |
| $C_{10-12}$ Dimethyl hydroxyethylammonium chloride | 0.75 | 0.94 | 0.98 | 0.98 | 0 | 0 |
| Crystalline layered silicate (δ-$Na_2Si_2O_5$) | 4.1 | 0 | 4.8 | 0 | 0 | 0 |
| Zeolite A | 5 | 0 | 5 | 0 | 2 | 2 |
| Citric Acid | 3 | 5 | 3 | 4 | 2.5 | 3 |
| Sodium Carbonate | 15 | 20 | 14 | 20 | 23 | 23 |
| Silicate 2R ($SiO_2$:$Na_2O$ at ratio 2:1) | 0.08 | 0 | 0.11 | 0 | 0 | 0 |
| Soil release agent | 0.75 | 0.72 | 0.71 | 0.72 | 0 | 0 |
| Acrylic Acid/Maleic Acid Copolymer | 1.1 | 3.7 | 1.0 | 3.7 | 2.6 | 3.8 |
| Carboxymethylcellulose | 0.15 | 1.4 | 0.2 | 1.4 | 1 | 0.5 |
| Protease-Purafect ® (84 mg active/g) | 0.2 | 0.2 | 0.3 | 0.15 | 0.12 | 0.13 |
| Lipase-Lipex ® (18.00 mg active/g) | 0.05 | 0.15 | 0.1 | 0 | 0 | 0 |
| Cellulase-Celluclean ™ (15.6 mg active/g) | 0 | 0 | 0 | 0 | 0.1 | 0.1 |

-continued

|  | 7 (wt %) | 8 (wt %) | 9 (wt %) | 10 (wt %) | 11 (wt %) | 12 (wt %) |
|---|---|---|---|---|---|---|
| *Amylase of the present invention (mg active) | 4.0 | 2.0 | 1.0 | 0.7 | 6.0 | 3.0 |
| TAED | 3.6 | 4.0 | 3.6 | 4.0 | 2.2 | 1.4 |
| Percarbonate | 13 | 13.2 | 13 | 13.2 | 16 | 14 |
| Na salt of Ethylenediamine-N,N'-disuccinic acid, (S,S) isomer (EDDS) | 0.2 | 0.2 | 0.2 | 0.2 | 0.2 | 0.2 |
| Hydroxyethane di phosphonate (HEDP) | 0.2 | 0.2 | 0.2 | 0.2 | 0.2 | 0.2 |
| $MgSO_4$ | 0.42 | 0.42 | 0.42 | 0.42 | 0.4 | 0.4 |
| Perfume | 0.5 | 0.6 | 0.5 | 0.6 | 0.6 | 0.6 |
| Suds suppressor agglomerate | 0.05 | 0.1 | 0.05 | 0.1 | 0.06 | 0.05 |
| Soap | 0.45 | 0.45 | 0.45 | 0.45 | 0 | 0 |
| Sulphonated zinc phthalocyanine (active) | 0.0007 | 0.0012 | 0.0007 | 0 | 0 | 0 |
| S-ACMC | 0.01 | 0.01 | 0 | 0.01 | 0 | 0 |
| Direct Violet 9 (active) | 0 | 0 | 0.0001 | 0.0001 | 0 | 0 |
| Sulfate/Water & Miscellaneous | | | | Balance | | |

*Amylase of the present invention is shown as mgs of active enzyme per 100 g of detergent.

Examples 13-18

Heavy Duty Liquid Laundry Detergent Compositions

|  | 13 (wt %) | 14 (wt %) | 15 (wt %) | 16 (wt %) | 17 (wt %) | 18 (wt %) |
|---|---|---|---|---|---|---|
| $C_{12-15}$ Alkylethoxy(1.8)sulfate | 14.7 | 11.6 | | 16.31 | | 17.29 |
| $C_{11.8}$ Alkylbenzene sulfonate | 4.3 | 11.6 | 8.3 | 7.73 | 11.7 | 7.73 |
| $C_{16-17}$ Branched alkyl sulfate | 1.7 | 1.29 | | 3.09 | | 3.3 |
| $C_{12-14}$ Alkyl-9-ethoxylate | 0.9 | 1.07 | | 1.31 | | 1.31 |
| $C_{12}$ dimethylamine oxide | 0.6 | 0.64 | | 1.03 | | 1.03 |
| Citric acid | 3.5 | 0.65 | 3 | 0.66 | 2.27 | 0.67 |
| $C_{12-18}$ fatty acid | 1.5 | 2.32 | 3.6 | 1.52 | 0.82 | 1.52 |
| Sodium Borate (Borax) | 2.5 | 2.46 | 1.2 | 2.53 | | 2.53 |
| Sodium $C_{12-14}$ alkyl ethoxy 3 sulfate | | | 2.9 | | 3.9 | |
| $C_{14-15}$ alkyl 7-ethoxylate | | | 4.2 | | 1.9 | |
| $C_{12-14}$ Alkyl -7-ethoxylate | | | 1.7 | | 0.5 | |
| Ca chloride dihydrate | | | | | 0.045 | |
| Ca formate | 0.09 | 0.09 | | 0.09 | | 0.09 |
| A compound: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n); n is 20 to 30; x is 3 to 8, optionally sulphated or sulphonated | | | 1.2 | | 0.66 | |
| Random graft co-polymer[1] | | 1.46 | 0.5 | | 0.83 | |
| Ethoxylated Polyethylenimine [2] | 1.5 | 1.29 | | 1.44 | | 1.44 |
| Diethylene triamine pentaacetic acid | 0.34 | 0.64 | | 0.34 | | 0.34 |
| Diethylene triamine penta (methylene phosphonic acid) | | | 0.3 | | 0.3 | |
| 1-hydroxyethyidene-1,1-diphosphonic acid | | | | | 0.18 | |
| Dihydroxybenzene-3,5-disulfonic acid disodium salt hydrate | | | | | 0.19 | |
| Tinopal AMS-GX | | 0.06 | | | | 0.29 |
| Tinopal CBS-X | 0.2 | 0.17 | | 0.29 | | |
| Tinopal TAS-X B36 | | | | | 0.091 | |
| Amphiphilic alkoxylated grease cleaning polymer [3] | 1.28 | 1 | 0.4 | 1.93 | | 1.93 |
| Ethanol | 2 | 1.58 | 1.6 | 5.4 | 1.2 | 3.57 |
| Propylene Glycol | 3.9 | 3.59 | 1.3 | 4.3 | | 3.8 |
| Diethylene glycol | 1.05 | 1.54 | | 1.15 | | 1.15 |
| Polyethylene glycol | 0.06 | 0.04 | | 0.1 | | 0.1 |
| *Amylase of the present invention (mg active) | 15.0 | 10.0 | 5.0 | 8.0 | 4.25 | 11.7 |
| Monoethanolamine | 3.05 | 2.41 | 0.4 | 1.26 | 0.31 | 1.13 |
| NaOH | 2.44 | 1.8 | | 3.01 | 3.84 | 0.24 |
| Sodium Cumene Sulphonate | | | 1 | | 0.95 | |

-continued

| | 13 (wt %) | 14 (wt %) | 15 (wt %) | 16 (wt %) | 17 (wt %) | 18 (wt %) |
|---|---|---|---|---|---|---|
| Sodium Formate | | 0.11 | | 0.09 | 0.2 | 0.12 |
| Water, Aesthetics (Dyes, perfumes) and Minors (Enzymes, solvents, structurants) | | | balance | | | |

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Polyethylenimine (MW = 600) with 20 ethoxylate groups per —NH.
[3] Amphiphilic alkoxylated grease cleaning polymer is a polyethylenimine (MW = 600) with 24 ethoxylate groups per —NH and 16 propoxylate groups per —NH
*Amylase of the present invention is shown as mgs of active enzyme per 100 g of detergent.

Examples 19-21

Heavy Duty Liquid Laundry Detergent Composition

| | 19 (wt %) | 20 (wt %) | 21 (wt %) |
|---|---|---|---|
| Sodium Alkylbenzene sulfonate | 21.0 | 10.2 | 3.53 |
| $C_{124-18}$ Alkyl 1.5-9-ethoxylate | 18.0 | 6.32 | 0.88 |
| Branched Alkyl Sulfate | | | 2.44 |
| Sodium Alkyl ethoxy 1-3 sulfate | | 1.17 | 14.81 |
| Citric Acid | | 3.14 | 2.05 |
| $C_{12}$ Dimethylamine oxide | | | 0.56 |
| $C_{12-18}$ Fatty acid | 15.0 | 2.59 | 1.48 |
| Protease (Purafect Prime ®, 40.6 mg active/g) | 1.5 | 0.52 | 1.64 |
| Mannanase (Mannaway ®, 11 mg active/g) | 0.1 | 0.06 | |
| Xyloglucanase (Whitezyme ®, 20 mg active/g) | 0.2 | 0.06 | |
| *Amylase of the present invention (mg active) | 5.9 | 2.3 | 12.8 |
| $bis((C_2H_5O)(C_2H_4O)n)(CH_3)$—$N^+$—$C_xH_{2x}$—$N^+$—$(CH_3)$—$bis((C_2H_5O)(C_2H_4O)n)$, wherein n = from 20 to 30, and x = from 3 to 8, optionally sulphated or sulphonated | 2.0 | 0.63 | |
| Random graft co-polymer[1] | | 1.07 | |
| Ethoxylated Polyethylenimine[2] | 0.8 | | 1.51 |
| Amphiphilic alkoxylated polymer[3] | | | |
| Phosphonated chelant | 0.8 | 0.41 | 0.53 |
| Hydrotrope | | 0.93 | |
| Brightener | 0.2 | 0.09 | 0.19 |
| Ethoxylated thiophene Hueing Dye | 0.004 | | |
| Minors: dyes, perfume, perfume micro capsules, enzymes, enzyme stabilizers, solvents, structurants, pH modifying agents | Balance | Balance | Balance |

*Amylase of the present invention is shown as mgs of active enzyme per 100 g of detergent.
**Based on total cleaning and/or treatment composition weight, a total of no more than 7% water.
[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Polyethyleneimine (MW = 600) with 20 ethoxylate groups per —NH.
[3] Amphiphilic alkoxylated polymer is a polyethylenimine (MW 600), prepared from a polymer that is derivatised to contain 24 ethoxylate groups per —NH and 16 Propoxylate groups per —NH.

Raw Materials and Notes For Composition Examples 1-21

Linear alkylbenzenesulfonate having an average aliphatic carbon chain length $C_{11}$-$C_{18}$
$C_{12-18}$ Dimethylhydroxyethyl ammonium chloride
AE3S is $C_{12-15}$ alkyl ethoxy (3) sulfate
AE7 is $C_{12-15}$ alcohol ethoxylate, with an average degree of ethoxylation of 7
AE9 is $C_{12-16}$ alcohol ethoxylate, with an average degree of ethoxylation of 9
HSAS is a mid-branched primary alkyl sulfate with carbon chain length of about 16-17 as disclosed in U.S. Pat. No. 6,020,303 and U.S. Pat. No. 6,060,443
Polyacrylate MW 4500 is supplied by BASF
Carboxymethyl cellulose is Finnfix® V supplied by CP Kelco, Arnhem, Netherlands
Phosphonate chelants are, for example, diethylenetetraamine pentaacetic acid (DTPA)
Hydroxyethane di phosphonate (HEDP)
Savinase®, Natalase®, Stainzyme®, Lipex®, Celluclean™, Mannaway® and Whitezyme® are all products of Novozymes, Bagsvaerd, Denmark.
Purafect®, Purafect Prime® are products of Genencor International, Palo Alto, Calif., USA
Fluorescent Brightener 1 is Tinopal® AMS, Fluorescent Brightener 2 is Tinopal® CBS-X, Direct Violet 9 is Pergasol® Violet BN-Z NOBS is sodium nonanoyloxybenzenesulfonate
TAED is tetraacetylethylenediamine
S-ACMC is carboxymethylcellulose conjugated with C.I. Reactive Blue 19product name AZO-CM-CELLULOSE
Soil release agent is Repel-o-tex® PF
Acrylic Acid/Maleic Acid Copolymer is molecular weight 70,000 and acrylate:maleate ratio 70:30
EDDS is a sodium salt of ethylenediamine-N,N'-disuccinic acid, (S,S) isomer Suds suppressor agglomerate is supplied by Dow Corning, Midland, Mich., USA
HSAS is mid-branched alkyl sulfate
Liquitint® Violet CT is supplied by Milliken, Spartanburg, S.C., USA Examples 22-26

Unit Dose Laundry Detergent Compositions. Such Unit Dose Formulations Can Comprise One or Multiple Compartments

| | 22 (wt %) | 23 (wt %) | 24 (wt %) | 25 (wt %) | 26 (wt %) |
|---|---|---|---|---|---|
| Alkylbenzene sulfonic acid | 14.5 | 14.5 | 14.5 | 14.5 | 14.5 |
| $C_{12-18}$ alkyl ethoxy 3 sulfate | 7.5 | 7.5 | 7.5 | 7.5 | 7.5 |
| $C_{12-18}$ alkyl 7-ethoxylate | 13.0 | 13.0 | 13.0 | 13.0 | 13.0 |
| Citric Acid | 0.6 | 0.6 | 0.6 | 0.6 | 0.6 |
| Fatty Acid | 14.8 | 14.8 | 14.8 | 14.8 | 14.8 |
| *Amylase of this invention (mg active) | 6 | 12 | 8 | 2 | 10 |
| Ethoxylated Polyethylenimine[1] | 4.0 | 4.0 | 4.0 | 4.0 | 4.0 |

-continued

| | 22 (wt %) | 23 (wt %) | 24 (wt %) | 25 (wt %) | 26 (wt %) |
|---|---|---|---|---|---|
| Protease (Purafect Prime ®, 40.6 mg active/g) | 1.4 | 2.0 | 0.9 | 1.2 | 0 |
| Hydroxyethane diphosphonic acid | 1.2 | 1.2 | 1.2 | 1.2 | 1.2 |
| Brightener | 0.3 | 0.3 | 0.3 | 0.3 | 0.3 |
| P-diol | 15.8 | 13.8 | 13.8 | 13.8 | 13.8 |
| Glycerol | 6.1 | 6.1 | 6.1 | 6.1 | 6.1 |
| MEA | 8.0 | 8.0 | 8.0 | 8.0 | 8.0 |
| TIPA | — | — | 2.0 | — | — |
| TEA | — | 2.0 | — | — | — |
| Cumene sulphonate | — | — | — | — | 2.0 |
| cyclohexyl dimethanol | — | — | — | 2.0 | — |
| Water | 10 | 10 | 10 | 10 | 10 |
| Structurant | 0.14 | 0.14 | 0.14 | 0.14 | 0.14 |
| Perfume | 1.9 | 1.9 | 1.9 | 1.9 | 1.9 |
| Buffers (monoethanolamine) | | | To pH 8.0 | | |
| Solvents (1,2 propanediol, ethanol) | | | To 100% | | |

*Amylase of the present invention is shown as mgs of active enzyme per 100 g of detergent.
[1]Polyethylenimine (MW = 600) with 20 ethoxylate groups per —NH.

Example 27

Multiple Compartment Unit Dose Composition

Multiple compartment unit dose laundry detergent formulations of the present invention are provided below. In these examples the unit dose has three compartments, but similar compositions can be made with two, four or five compartments. The film used to encapsulate the compartments is polyvinyl alcohol.

| Base composition 1 | 27 (wt %) |
|---|---|
| Glycerol (min 99) | 5.3 |
| 1,2-propanediol | 10.0 |
| Citric Acid | 0.5 |
| Monoethanolamine | 10.0 |
| Caustic soda | — |
| Dequest 2010 | 1.1 |
| Potassium sulfite | 0.2 |
| *Amylase of this invention (mg active) | 8.0 |
| Nonionic Marlipal C24EO7 | 20.1 |
| HLAS | 24.6 |
| Optical brightener FWA49 | 0.2 |
| C12-15 Fatty acid | 16.4 |
| Polymer Lutensit Z96 | 2.9 |
| Polyethyleneimine ethoxylate PEI600 E20 | 1.1 |
| MgCl2 | 0.2 |
| Solvents (1,2 propanediol, ethanol) | To 100% |

Multi-Compartment Formulations

| Composition | 1 | | | 2 | | |
|---|---|---|---|---|---|---|
| Compartment | A | B | C | A | B | C |
| Volume of each compartment | 40 ml | 5 ml | 5 ml | 40 ml | 5 ml | 5 ml |
| Active material in Wt. % | | | | | | |
| Perfume | 1.6 | 1.6 | 1.6 | 1.6 | 1.6 | 1.6 |
| Dyes | <0.01 | <0.01 | <0.01 | <0.01 | <0.01 | <0.01 |
| TiO2 | 0.1 | — | — | — | 0.1 | — |
| Sodium Sulfite | 0.4 | 0.4 | 0.4 | 0.3 | 0.3 | 0.3 |
| Acusol 305 | 1.2 | — | — | 2 | — | — |
| Hydrogenated castor oil | 0.14 | 0.14 | 0.14 | 0.14 | 0.14 | 0.14 |
| Base Composition 1 | Add to 100% | Add to 100% | Add to 100% | Add to 100% | Add to 100% | Add to 100% |

*Amylase of the present invention is shown as mgs of active enzyme per 100 g of detergent.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

"Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern."

"While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention."

What is claimed is:

1. A cleaning composition comprising:
   (a) a variant of a alpha-amylase wherein the variant has at least 80%, but less than 100% sequence identity with the mature alpha-amylase polypeptide comprising SEQ ID NO:1 and wherein the variant comprises an amino acid substitution selected from the group consisting of G477E, G477Q, G477K, G477M, and G477R corresponding to position G477 of said SEQ ID NO: 1 and further comprises an amino acid sequence alteration at one or more positions: D134, W140, W189, E260, F262, W284, G304, W347, W439, W469, and G476 of said SEQ ID NO: 1, wherein each alteration is independently an amino acid substitution, deletion or insertion, and wherein the variant has alpha-amylase activity; and
   (b) a cleaning adjunct, in an amount from 0.01 to 99.9 wt %.

2. A composition according to claim 1, wherein the further amino acid sequence alteration is a substitution.

3. A composition according to claim 1, wherein the variant comprises the substitution which is selected from the group consisting of G304, W140, W189, D134, E260, F262, W284, W347, W439, W469, G476, and G477.

4. A composition according to claim 1, wherein the variant comprises the substitution selected from the group consisting of G304, W140, W189, D134, E260, F262, W284, W347, W439, W469, G476, and G477.

5. A composition according to claim 1, wherein the variant comprises the substitution which is selected from the group consisting of G304, W140, E260, G476, and G477.

6. A composition according to claim 1, wherein the variant comprises a substitution selected from the group consisting of G477E, G477K, G477M, and G477R and further comprises one or more substitutions selected from the group consisting of G304R, W140Y, W140F, W189E, W189G, W189T, D134E, E260G, E260H, E260I, E260K, E260R, E260T, E260Y, W284D, W284F, W284R, W439R, W439G, G476E, and G476K.

7. A composition according to claim 1, wherein the variant comprises a substitution selected from the group consisting of G477E, G477K, G477M, and G477R and further comprises substitutions at one, two, or three positions selected from the group consisting of G304R, W140Y, W140F, E260G, E260H, E260I, E260K, E260R, E260T, E260Y, G476E, and G476K.

8. A composition according to claim 1, wherein the variant comprises a substitution selected from the group consisting of G477E, G477K, G477M, and G477R and further comprises substitutions at one, two, or three positions selected from the group consisting of G304R, W140Y, E260G and G476K.

9. A composition according to claim 1 wherein the variant comprises one or more substitutions selected from the group consisting of N195F, V206Y, Y243F, G109A, G273D, G273V, G337N, K72R, R181H, S303G and Y100I.

10. A composition according to claim 1 wherein the number of alterations in the variant is from 2 to 10.

11. A composition according to claim 1, wherein the variant alpha-amylase has at least 87%, but less than 100%, sequence identity with the mature polypeptide of SEQ ID NO:1.

12. A composition according to claim 1, wherein the variant comprises substitutions in said SEQ ID NO: 1, wherein said substitutions are selected from the group consisting of:
   W140Y+N195F+V206Y+Y243F+E260G+G547E,
   W140Y+N195F+V206Y+Y243F+E260G+W284R+G477K, and
   W140Y+N195F+V206Y+Y243F+E260G+W284F+G477R.

13. A composition according to claim 1, wherein the variant consists of substitutions in said SEQ ID NO: 1, wherein said substitutions are selected from the group consisting of:
   W140Y+N195F+V206Y+Y243F+E260G+G547E,
   W140Y+N195F+V206Y+Y243F+E260G+W284R+647K, and
   W140Y+N195F+V206Y+Y243F+E260G±W284F+G477R.

14. A composition according to claim 1, wherein the variant comprises alterations in said SEQ ID NO: 1, wherein said substitutions are selected from the group consisting of:
   D183*+G184*+W140Y+N195F+V206Y+Y243F+E260G+G477E,
   D183*+G184*+W140Y+N195F+V206Y+Y243F+E260G+W284R+G477K, and
   D183*+G184*+W140Y+N195F+V206Y+Y243F+E260G+W284F+G477R.

15. A composition according to claim 1, wherein the variant consists of alterations in said SEQ ID NO: 1, wherein said substitutions are selected from the group consisting of:
   D183*+G184*+W140Y+N195F+V206Y+Y243F+E260G+G477E,
   D183*+G184*+W140Y+N195F+V206Y+Y243F+E260G+W284R+G477K, and
   D183*+G184*+W140Y+N195F+V206Y+Y243F+E260G+W284F+G477R.

16. A composition according to claim 1, wherein the variant further comprises deletions in said SEQ ID NO:1 wherein said deletions are selected from the group consisting of G182*+D183* and D183*+G184*.

17. A composition according to claim 1, wherein the variant further comprises substitutions in said SEQ ID NO:1 wherein said substitutions are N195F+V206Y+Y243F.

18. A composition according to claim 1, wherein the cleaning adjunct comprises one or more selected from the group consisting of (i) a perfume microcapsule; (ii) a fabric hueing agent; (iii) a protease; (iv) an amphiphilic cleaning polymer; (v) a lipase, and (vi) mixtures thereof.

19. A composition according to claim 1, wherein the composition is a liquid laundry detergent composition or unit dose detergent composition.

20. A method of treating a textile, comprising:
(i) forming an aqueous wash liquor comprising water and a composition according to claim 1;
(ii) treating the surface with the aqueous wash liquor at a temperature of 40° C. or less; and
(iii) rinsing the surface.

* * * * *

SEQUENCE LISTING

```
<160> NUMBER OF SEQ ID NOS: 12

<210> SEQ ID NO 1
<211> LENGTH: 485
<212> TYPE: PRT
<213> ORGANISM: Bacillus sp.

<400> SEQUENCE: 1

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
```

```
                    20                  25                  30
Asn Leu Arg Asn Arg Gly Ile Thr Ala Ile Trp Ile Pro Pro Ala Trp
                35                  40                  45

Lys Gly Thr Ser Gln Asn Asp Val Gly Tyr Gly Ala Tyr Asp Leu Tyr
         50                  55                  60

Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
                 85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
                115                 120                 125

Gln Glu Ile Ser Gly Asp Tyr Thr Ile Glu Ala Trp Thr Lys Phe Asp
                130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
                180                 185                 190

Ser Glu Asn Gly Asn Tyr Asp Tyr Leu Met Tyr Ala Asp Val Asp Met
                195                 200                 205

Asp His Pro Glu Val Val Asn Glu Leu Arg Arg Trp Gly Glu Trp Tyr
                210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
                260                 265                 270

Gly Ala Leu Glu Asn Tyr Leu Asn Lys Thr Asn Trp Asn His Ser Val
                275                 280                 285

Phe Asp Val Pro Leu His Tyr Asn Leu Tyr Asn Ala Ser Asn Ser Gly
                290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
                340                 345                 350

Tyr Ala Leu Ile Leu Thr Arg Glu Gln Gly Tyr Pro Ser Val Phe Tyr
                355                 360                 365

Gly Asp Tyr Tyr Gly Ile Pro Thr His Ser Val Pro Ala Met Lys Ala
                370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
                420                 425                 430

Gly Pro Gly Gly Glu Lys Trp Met Tyr Val Gly Gln Asn Lys Ala Gly
                435                 440                 445
```

```
Gln Val Trp His Asp Ile Thr Gly Asn Lys Pro Gly Thr Val Thr Ile
            450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
```

```
                    325                 330                 335
Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Arg Ser
        370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
        450                 455                 460

Asn Ala Asp Gly Trp Gly Asn Phe Ser Val Asn Gly Ser Val Ser
465                 470                 475                 480

Ile Trp Val Asn Lys
                485

<210> SEQ ID NO 3
<211> LENGTH: 485
<212> TYPE: PRT
<213> ORGANISM: Bacillus sp.

<400> SEQUENCE: 3

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205
```

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
            275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 4
<211> LENGTH: 485
<212> TYPE: PRT
<213> ORGANISM: Bacillus sp.

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

```
Ile Gln Val Tyr Gly Asp Val Met Asn His Lys Gly Gly Ala Asp
            100                 105                 110
Gly Thr Glu Ile Val Asn Ala Val Glu Val Asn Arg Ser Asn Arg Asn
        115                 120                 125
Gln Glu Thr Ser Gly Glu Tyr Ala Ile Glu Ala Trp Thr Lys Phe Asp
130                 135                 140
Phe Pro Gly Arg Gly Asn Asn His Ser Ser Phe Lys Trp Arg Trp Tyr
145                 150                 155                 160
His Phe Asp Gly Thr Asp Trp Asp Gln Ser Arg Gln Leu Gln Asn Lys
                165                 170                 175
Ile Tyr Lys Phe Arg Gly Thr Gly Lys Ala Trp Asp Trp Glu Val Asp
            180                 185                 190
Thr Glu Asn Gly Asn Tyr Asp Tyr Leu Met Tyr Ala Asp Val Asp Met
        195                 200                 205
Asp His Pro Glu Val Ile His Glu Leu Arg Asn Trp Gly Val Trp Tyr
210                 215                 220
Thr Asn Thr Leu Asn Leu Asp Gly Phe Arg Ile Asp Ala Val Lys His
225                 230                 235                 240
Ile Lys Tyr Ser Phe Thr Arg Asp Trp Leu Thr His Val Arg Asn Thr
                245                 250                 255
Thr Gly Lys Pro Met Phe Ala Val Ala Glu Phe Trp Lys Asn Asp Leu
            260                 265                 270
Gly Ala Ile Glu Asn Tyr Leu Asn Lys Thr Ser Trp Asn His Ser Val
        275                 280                 285
Phe Asp Val Pro Leu His Tyr Asn Leu Tyr Asn Ala Ser Asn Ser Gly
290                 295                 300
Gly Tyr Tyr Asp Met Arg Asn Ile Leu Asn Gly Ser Val Val Gln Lys
305                 310                 315                 320
His Pro Thr His Ala Val Thr Phe Val Asp Asn His Asp Ser Gln Pro
                325                 330                 335
Gly Glu Ala Leu Glu Ser Phe Val Gln Gln Trp Phe Lys Pro Leu Ala
            340                 345                 350
Tyr Ala Leu Val Leu Thr Arg Glu Gln Gly Tyr Pro Ser Val Phe Tyr
        355                 360                 365
Gly Asp Tyr Tyr Gly Ile Pro Thr His Gly Val Pro Ala Met Lys Ser
370                 375                 380
Lys Ile Asp Pro Leu Leu Gln Ala Arg Gln Thr Phe Ala Tyr Gly Thr
385                 390                 395                 400
Gln His Asp Tyr Phe Asp His His Asp Ile Ile Gly Trp Thr Arg Glu
                405                 410                 415
Gly Asn Ser Ser His Pro Asn Ser Gly Leu Ala Thr Ile Met Ser Asp
            420                 425                 430
Gly Pro Gly Gly Asn Lys Trp Met Tyr Val Gly Lys Asn Lys Ala Gly
        435                 440                 445
Gln Val Trp Arg Asp Ile Thr Gly Asn Arg Thr Gly Thr Val Thr Ile
450                 455                 460
Asn Ala Asp Gly Trp Gly Asn Phe Ser Val Asn Gly Gly Ser Val Ser
465                 470                 475                 480
Val Trp Val Lys Gln
                485

<210> SEQ ID NO 5
<211> LENGTH: 485
```

<212> TYPE: PRT
<213> ORGANISM: Bacillus sp.

<400> SEQUENCE: 5

```
His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
        115                 120                 125

Gln Glu Ile Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Ile Glu Asn Gly Asn Tyr Asp Tyr Leu Met Tyr Ala Asp Ile Asp Met
        195                 200                 205

Asp His Pro Glu Val Ile Asn Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Ala Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Phe Asp Met Arg Asn Ile Leu Asn Gly Ser Val Val Gln Lys
305                 310                 315                 320

His Pro Ile His Ala Val Thr Phe Val Asp Asn His Asp Ser Gln Pro
                325                 330                 335

Gly Glu Ala Leu Glu Ser Phe Val Gln Ser Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Gly Val Pro Ser Met Lys Ser
    370                 375                 380

Lys Ile Asp Pro Leu Leu Gln Ala Arg Gln Thr Tyr Ala Tyr Gly Thr
385                 390                 395                 400
```

```
Gln His Asp Tyr Phe Asp His Asp Ile Ile Gly Trp Thr Arg Glu
            405                 410                 415

Gly Asp Ser Ser His Pro Asn Ser Gly Leu Ala Thr Ile Met Ser Asp
        420                 425                 430

Gly Pro Gly Gly Asn Lys Trp Met Tyr Val Gly Lys His Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Thr Val Asn Gly Gly Ala Val Ser
465                 470                 475                 480

Val Trp Val Lys Gln
            485

<210> SEQ ID NO 6
<211> LENGTH: 485
<212> TYPE: PRT
<213> ORGANISM: Bacillus sp.

<400> SEQUENCE: 6

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
```

```
                275                 280                 285
Phe Asp Val Pro Leu His Tyr Asn Leu Tyr Asn Ala Ser Arg Ser Gly
290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Trp Phe Lys Pro Leu Ala
                340                 345                 350

Tyr Ala Leu Thr Leu Thr Arg Asp Gln Gly Tyr Pro Ser Val Phe Tyr
                355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
                420                 425                 430

Gly Pro Gly Gly Asn Lys Trp Met Tyr Val Gly Arg Asn Lys Ala Gly
                435                 440                 445

Gln Val Trp Arg Asp Ile Thr Gly Asn Arg Ser Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Asn
                485

<210> SEQ ID NO 7
<211> LENGTH: 483
<212> TYPE: PRT
<213> ORGANISM: Bacillus sp.

<400> SEQUENCE: 7

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
                35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
                115                 120                 125

Gln Glu Ile Ser Gly Asp Tyr Thr Ile Glu Ala Trp Thr Lys Phe Asp
                130                 135                 140

Phe Pro Gly Arg Gly Asn Thr Tyr Ser Asp Phe Lys Trp Arg Trp Tyr
145                 150                 155                 160
```

His Phe Asp Gly Val Asp Trp Asp Gln Ser Arg Gln Phe Gln Asn Arg
             165                 170                 175

Ile Tyr Lys Phe Arg Gly Lys Ala Trp Asp Trp Glu Val Asp Ser Glu
         180                 185                 190

Asn Gly Asn Tyr Asp Tyr Leu Met Tyr Ala Asp Val Asp Met Asp His
             195                 200                 205

Pro Glu Val Val Asn Glu Leu Arg Arg Trp Gly Glu Trp Tyr Thr Asn
         210                 215                 220

Thr Leu Asn Leu Asp Gly Phe Arg Ile Asp Ala Val Lys His Ile Lys
225                 230                 235                 240

Tyr Ser Phe Thr Arg Asp Trp Leu Thr His Val Arg Asn Ala Thr Gly
             245                 250                 255

Lys Glu Met Phe Ala Val Ala Glu Phe Trp Lys Asn Asp Leu Gly Ala
         260                 265                 270

Leu Glu Asn Tyr Leu Asn Lys Thr Asn Trp Asn His Ser Val Phe Asp
             275                 280                 285

Val Pro Leu His Tyr Asn Leu Tyr Asn Ala Ser Asn Ser Gly Gly Asn
         290                 295                 300

Tyr Asp Met Ala Lys Leu Leu Asn Gly Thr Val Val Gln Lys His Pro
305                 310                 315                 320

Met His Ala Val Thr Phe Val Asp Asn His Asp Ser Gln Pro Gly Glu
             325                 330                 335

Ser Leu Glu Ser Phe Val Gln Glu Trp Phe Lys Pro Leu Ala Tyr Ala
         340                 345                 350

Leu Ile Leu Thr Arg Glu Gln Gly Tyr Pro Ser Val Phe Tyr Gly Asp
             355                 360                 365

Tyr Tyr Gly Ile Pro Thr His Ser Val Pro Ala Met Lys Ala Lys Ile
         370                 375                 380

Asp Pro Ile Leu Glu Ala Arg Gln Asn Phe Ala Tyr Gly Thr Gln His
385                 390                 395                 400

Asp Tyr Phe Asp His His Asn Ile Ile Gly Trp Thr Arg Glu Gly Asn
             405                 410                 415

Thr Thr His Pro Asn Ser Gly Leu Ala Thr Ile Met Ser Asp Gly Pro
         420                 425                 430

Gly Gly Glu Lys Trp Met Tyr Val Gly Gln Asn Lys Ala Gly Gln Val
             435                 440                 445

Trp His Asp Ile Thr Gly Asn Lys Pro Gly Thr Val Thr Ile Asn Ala
         450                 455                 460

Asp Gly Trp Ala Asn Phe Ser Val Asn Gly Gly Ser Val Ser Ile Trp
465                 470                 475                 480

Val Lys Arg

<210> SEQ ID NO 8
<211> LENGTH: 483
<212> TYPE: PRT
<213> ORGANISM: Bacillus sp.

<400> SEQUENCE: 8

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
             20                  25                  30

Asn Leu Lys Ser Lys Gly Ile Thr Ala Val Trp Ile Pro Pro Ala Trp
         35                  40                  45

-continued

```
Lys Gly Ala Ser Gln Asn Asp Val Gly Tyr Gly Ala Tyr Asp Leu Tyr
 50                  55                  60
Asp Leu Gly Glu Phe Asn Gln Lys Gly Thr Val Arg Thr Lys Tyr Gly
 65                  70                  75                  80
Thr Arg Ser Gln Leu Gln Ala Ala Val Thr Ser Leu Lys Asn Asn Gly
                 85                  90                  95
Ile Gln Val Tyr Gly Asp Val Val Met Asn His Lys Gly Gly Ala Asp
                100                 105                 110
Ala Thr Glu Met Val Arg Ala Val Glu Val Asn Pro Asn Asn Arg Asn
            115                 120                 125
Gln Glu Val Thr Gly Glu Tyr Thr Ile Glu Ala Trp Thr Arg Phe Asp
130                 135                 140
Phe Pro Gly Arg Gly Asn Thr His Ser Ser Phe Lys Trp Arg Trp Tyr
145                 150                 155                 160
His Phe Asp Gly Val Asp Trp Asp Gln Ser Arg Arg Leu Asn Asn Arg
                165                 170                 175
Ile Tyr Lys Phe Arg Gly Lys Ala Trp Asp Trp Glu Val Asp Thr Glu
                180                 185                 190
Asn Gly Asn Tyr Asp Tyr Leu Met Tyr Ala Asp Ile Asp Met Asp His
            195                 200                 205
Pro Glu Val Val Asn Glu Leu Arg Asn Trp Gly Val Trp Tyr Thr Asn
210                 215                 220
Thr Leu Gly Leu Asp Gly Phe Arg Ile Asp Ala Val Lys His Ile Lys
225                 230                 235                 240
Tyr Ser Phe Thr Arg Asp Trp Ile Asn His Val Arg Ser Ala Thr Gly
                245                 250                 255
Lys Asn Met Phe Ala Val Ala Glu Phe Trp Lys Asn Asp Leu Gly Ala
            260                 265                 270
Ile Glu Asn Tyr Leu Gln Lys Thr Asn Trp Asn His Ser Val Phe Asp
        275                 280                 285
Val Pro Leu His Tyr Asn Leu Tyr Asn Ala Ser Lys Ser Gly Gly Asn
290                 295                 300
Tyr Asp Met Arg Asn Ile Phe Asn Gly Thr Val Val Gln Arg His Pro
305                 310                 315                 320
Ser His Ala Val Thr Phe Val Asp Asn His Asp Ser Gln Pro Glu Glu
                325                 330                 335
Ala Leu Glu Ser Phe Val Glu Trp Phe Lys Pro Leu Ala Tyr Ala
            340                 345                 350
Leu Thr Leu Thr Arg Glu Gln Gly Tyr Pro Ser Val Phe Tyr Gly Asp
        355                 360                 365
Tyr Tyr Gly Ile Pro Thr His Gly Val Pro Ala Met Arg Ser Lys Ile
    370                 375                 380
Asp Pro Ile Leu Glu Ala Arg Gln Lys Tyr Ala Tyr Gly Lys Gln Asn
385                 390                 395                 400
Asp Tyr Leu Asp His His Asn Ile Ile Gly Trp Thr Arg Glu Gly Asn
                405                 410                 415
Thr Ala His Pro Asn Ser Gly Leu Ala Thr Ile Met Ser Asp Gly Ala
            420                 425                 430
Gly Gly Ser Lys Trp Met Phe Val Gly Arg Asn Lys Ala Gly Gln Val
        435                 440                 445
Trp Ser Asp Ile Thr Gly Asn Arg Thr Gly Thr Val Thr Ile Asn Ala
    450                 455                 460
Asp Gly Trp Gly Asn Phe Ser Val Asn Gly Gly Ser Val Ser Ile Trp
```

465                 470                 475                 480

Val Asn Lys

<210> SEQ ID NO 9
<211> LENGTH: 483
<212> TYPE: PRT
<213> ORGANISM: Bacillus sp.

<400> SEQUENCE: 9

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Lys Gly Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Gln Ile Phe Asn Gly Thr Val Val Gln Arg His Pro
305                 310                 315                 320

Met His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp

```
            355                 360                 365
Tyr Tyr Gly Ile Pro Thr His Gly Val Pro Ala Met Lys Ser Lys Ile
            370                 375                 380

Asp Pro Ile Leu Glu Ala Arg Gln Lys Tyr Ala Tyr Gly Arg Gln Asn
385                 390                 395                 400

Asp Tyr Leu Asp His Asn Ile Ile Gly Trp Thr Arg Glu Gly Asn
                405                 410                 415

Thr Ala His Pro Asn Ser Gly Leu Ala Thr Ile Met Ser Asp Gly Ala
                420                 425                 430

Gly Gly Asn Lys Trp Met Phe Val Gly Arg Asn Lys Ala Gly Gln Val
            435                 440                 445

Trp Thr Asp Ile Thr Gly Asn Arg Ala Gly Thr Val Thr Ile Asn Ala
            450                 455                 460

Asp Gly Trp Gly Asn Phe Ser Val Asn Gly Gly Ser Val Ser Ile Trp
465                 470                 475                 480

Val Asn Lys

<210> SEQ ID NO 10
<211> LENGTH: 483
<212> TYPE: PRT
<213> ORGANISM: Bacillus sp.

<400> SEQUENCE: 10

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
        115                 120                 125

Gln Glu Thr Ser Gly Glu Tyr Ala Ile Glu Ala Trp Thr Lys Phe Asp
    130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Tyr Ala Asp Val Asp Met Asp His
        195                 200                 205

Pro Glu Val Ile His Glu Leu Arg Asn Trp Gly Val Trp Tyr Thr Asn
    210                 215                 220

Thr Leu Asn Leu Asp Gly Phe Arg Ile Asp Ala Val Lys His Ile Lys
225                 230                 235                 240

Tyr Ser Phe Thr Arg Asp Trp Leu Thr His Val Arg Asn Thr Thr Gly
```

```
                    245                 250                 255
Lys Pro Met Phe Ala Val Ala Glu Phe Trp Lys Asn Asp Leu Gly Ala
            260                 265                 270

Ile Glu Asn Tyr Leu Asn Lys Thr Ser Trp Asn His Ser Val Phe Asp
                275                 280                 285

Val Pro Leu His Tyr Asn Leu Tyr Asn Ala Ser Asn Ser Gly Gly Tyr
            290                 295                 300

Tyr Asp Met Arg Asn Ile Leu Asn Gly Ser Val Val Gln Lys His Pro
305                 310                 315                 320

Thr His Ala Val Thr Phe Val Asp Asn His Asp Ser Gln Pro Gly Glu
                325                 330                 335

Ala Leu Glu Ser Phe Val Gln Gln Trp Phe Lys Pro Leu Ala Tyr Ala
            340                 345                 350

Leu Val Leu Thr Arg Glu Gln Gly Tyr Pro Ser Val Phe Tyr Gly Asp
                355                 360                 365

Tyr Tyr Gly Ile Pro Thr His Gly Val Pro Ala Met Lys Ser Lys Ile
            370                 375                 380

Asp Pro Leu Leu Gln Ala Arg Gln Thr Phe Ala Tyr Gly Thr Gln His
385                 390                 395                 400

Asp Tyr Phe Asp His His Asp Ile Ile Gly Trp Thr Arg Glu Gly Asn
                405                 410                 415

Ser Ser His Pro Asn Ser Gly Leu Ala Thr Ile Met Ser Asp Gly Pro
            420                 425                 430

Gly Gly Asn Lys Trp Met Tyr Val Gly Lys Asn Lys Ala Gly Gln Val
                435                 440                 445

Trp Arg Asp Ile Thr Gly Asn Arg Thr Gly Thr Val Thr Ile Asn Ala
            450                 455                 460

Asp Gly Trp Gly Asn Phe Ser Val Asn Gly Gly Ser Val Ser Val Trp
465                 470                 475                 480

Val Lys Gln

<210> SEQ ID NO 11
<211> LENGTH: 483
<212> TYPE: PRT
<213> ORGANISM: Bacillus sp.

<400> SEQUENCE: 11

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
        115                 120                 125

Gln Glu Ile Ser Gly Glu Tyr Thr Ile Glu Ala Trp Thr Lys Phe Asp
```

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
            165                 170                 175

Ile Tyr Lys Phe Arg Gly Lys Ala Trp Asp Trp Glu Val Asp Ile Glu
        180                 185                 190

Asn Gly Asn Tyr Asp Tyr Leu Met Tyr Ala Asp Ile Asp Met Asp His
    195                 200                 205

Pro Glu Val Ile Asn Glu Leu Arg Asn Trp Gly Val Trp Tyr Thr Asn
210                 215                 220

Thr Leu Asn Leu Asp Gly Phe Arg Ile Asp Ala Val Lys His Ile Lys
225                 230                 235                 240

Tyr Ser Tyr Thr Arg Asp Trp Leu Thr His Val Arg Asn Thr Thr Gly
                245                 250                 255

Lys Pro Met Phe Ala Val Ala Glu Phe Trp Lys Asn Asp Leu Ala Ala
            260                 265                 270

Ile Glu Asn Tyr Leu Asn Lys Thr Ser Trp Asn His Ser Val Phe Asp
        275                 280                 285

Val Pro Leu His Tyr Asn Leu Tyr Asn Ala Ser Asn Ser Gly Gly Tyr
    290                 295                 300

Phe Asp Met Arg Asn Ile Leu Asn Gly Ser Val Val Gln Lys His Pro
305                 310                 315                 320

Ile His Ala Val Thr Phe Val Asp Asn His Asp Ser Gln Pro Gly Glu
                325                 330                 335

Ala Leu Glu Ser Phe Val Gln Ser Trp Phe Lys Pro Leu Ala Tyr Ala
            340                 345                 350

Leu Ile Leu Thr Arg Glu Gln Gly Tyr Pro Ser Val Phe Tyr Gly Asp
        355                 360                 365

Tyr Tyr Gly Ile Pro Thr His Gly Val Pro Ser Met Lys Ser Lys Ile
    370                 375                 380

Asp Pro Leu Leu Gln Ala Arg Gln Thr Tyr Ala Tyr Gly Thr Gln His
385                 390                 395                 400

Asp Tyr Phe Asp His His Asp Ile Ile Gly Trp Thr Arg Glu Gly Asp
                405                 410                 415

Ser Ser His Pro Asn Ser Gly Leu Ala Thr Ile Met Ser Asp Gly Pro
            420                 425                 430

Gly Gly Asn Lys Trp Met Tyr Val Gly Lys His Lys Ala Gly Gln Val
        435                 440                 445

Trp Arg Asp Ile Thr Gly Asn Arg Ser Gly Thr Val Thr Ile Asn Ala
    450                 455                 460

Asp Gly Trp Gly Asn Phe Thr Val Asn Gly Gly Ala Val Ser Val Trp
465                 470                 475                 480

Val Lys Gln

<210> SEQ ID NO 12
<211> LENGTH: 483
<212> TYPE: PRT
<213> ORGANISM: Bacillus sp.

<400> SEQUENCE: 12

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser

-continued

```
            20                  25                  30
Asn Leu Lys Asp Lys Gly Ile Thr Ala Val Trp Ile Pro Ala Trp
            35                  40                  45
Lys Gly Ala Ser Gln Asn Asp Val Gly Tyr Gly Ala Tyr Asp Leu Tyr
        50                  55                  60
Asp Leu Gly Glu Phe Asn Gln Lys Gly Thr Val Arg Thr Lys Tyr Gly
 65                  70                  75                  80
Thr Arg Asn Gln Leu Gln Ala Ala Val Thr Ala Leu Lys Ser Asn Gly
                85                  90                  95
Ile Gln Val Tyr Gly Asp Val Val Met Asn His Lys Gly Gly Ala Asp
                100                 105                 110
Ala Thr Glu Trp Val Arg Ala Val Glu Val Asn Pro Ser Asn Arg Asn
            115                 120                 125
Gln Glu Val Ser Gly Asp Tyr Thr Ile Glu Ala Trp Thr Lys Phe Asp
            130                 135                 140
Phe Pro Gly Arg Gly Asn Thr His Ser Asn Phe Lys Trp Arg Trp Tyr
145                 150                 155                 160
His Phe Asp Gly Val Asp Trp Asp Gln Ser Arg Gln Leu Gln Asn Arg
                165                 170                 175
Ile Tyr Lys Phe Arg Gly Lys Gly Trp Asp Trp Glu Val Asp Thr Glu
                180                 185                 190
Asn Gly Asn Tyr Asp Tyr Leu Met Tyr Ala Asp Ile Asp Met Asp His
            195                 200                 205
Pro Glu Val Val Asn Glu Leu Arg Asn Trp Gly Val Trp Tyr Thr Asn
210                 215                 220
Thr Leu Gly Leu Asp Gly Phe Arg Ile Asp Ala Val Lys His Ile Lys
225                 230                 235                 240
Tyr Ser Phe Thr Arg Asp Trp Leu Thr His Val Arg Asn Thr Thr Gly
                245                 250                 255
Lys Asn Met Phe Ala Val Ala Glu Phe Trp Lys Asn Asp Ile Gly Ala
                260                 265                 270
Ile Glu Asn Tyr Leu Ser Lys Thr Asn Trp Asn His Ser Val Phe Asp
                275                 280                 285
Val Pro Leu His Tyr Asn Leu Tyr Asn Ala Ser Arg Ser Gly Gly Asn
            290                 295                 300
Tyr Asp Met Arg Gln Ile Phe Asn Gly Thr Val Val Gln Arg His Pro
305                 310                 315                 320
Thr His Ala Val Thr Phe Val Asp Asn His Asp Ser Gln Pro Glu Glu
                325                 330                 335
Ala Leu Glu Ser Phe Val Glu Glu Trp Phe Lys Pro Leu Ala Tyr Ala
            340                 345                 350
Leu Thr Leu Thr Arg Asp Gln Gly Tyr Pro Ser Val Phe Tyr Gly Asp
            355                 360                 365
Tyr Tyr Gly Ile Pro Thr His Gly Val Pro Ala Met Lys Ser Lys Ile
        370                 375                 380
Asp Pro Ile Leu Glu Ala Arg Gln Lys Tyr Ala Tyr Gly Lys Gln Asn
385                 390                 395                 400
Asp Tyr Leu Asp His His Asn Met Ile Gly Trp Thr Arg Glu Gly Asn
                405                 410                 415
Thr Ala His Pro Asn Ser Gly Leu Ala Thr Ile Met Ser Asp Gly Pro
            420                 425                 430
Gly Gly Asn Lys Trp Met Tyr Val Gly Arg Asn Lys Ala Gly Gln Val
            435                 440                 445
```

```
Trp Arg Asp Ile Thr Gly Asn Arg Ser Gly Thr Val Thr Ile Asn Ala
    450                 455                 460

Asp Gly Trp Gly Asn Phe Ser Val Asn Gly Gly Ser Val Ser Ile Trp
465                 470                 475                 480

Val Asn Asn
```